United States Patent [19]

Weber et al.

[11] Patent Number: 4,954,507

[45] Date of Patent: Sep. 4, 1990

[54] 1-TERTIARY-ALKYL-SUBSTITUTED NAPHTHYRIDINE CARBOXYLIC ACID ANTIBACTERIAL AGENTS

[75] Inventors: Abraham Weber, Sant-Mande; Daniel Bouzard, Franconville; Munir Essiz, Noisy le Granc; Pierre Di Cesare, Meaux; Jean-Pierre Jacquet, Menestreau-en-Villette; Philippe Remuzon, Paris, all of France

[73] Assignee: Bristol-Myers Company, New York, N.Y.

[21] Appl. No.: 287,502

[22] Filed: Dec. 19, 1988

Related U.S. Application Data

[63] Continuation of Ser. No. 99,231, Sep. 25, 1987, abandoned, which is a continuation-in-part of Ser. No. 916,752, Oct. 8, 1986, abandoned.

[51] Int. Cl.$^5$ .................. A61K 31/435; C07D 471/04
[52] U.S. Cl. ..................................... 514/300; 540/472; 540/500; 544/58.6; 544/127; 544/128; 544/349; 544/362; 544/363; 546/123; 546/156
[58] Field of Search ......................... 546/123; 514/300

[56] References Cited

U.S. PATENT DOCUMENTS 3,590,036 6/1971 Lesher et al. .................. 546/123
4,341,784 7/1982 Matsumoto et al. ............ 546/123

FOREIGN PATENT DOCUMENTS 132845 2/1985 European Pat. Off. .
153163 8/1985 European Pat. Off. .

OTHER PUBLICATIONS

Egawa et al., J. Med. Chem., 27, pp. 1543–1548, (1984).

*Primary Examiner*—John M. Ford
*Assistant Examiner*—Bernard I. Dentz
*Attorney, Agent, or Firm*—Robert E. Carnahan; Aldo A. Algieri

[57] ABSTRACT

There are disclosed new naphthyridine- and quinoline-carboxylic acids having a 1-tertiary-alkyl substituent, compositions containing them, and their use in treating bacterial infections in warm-blooded animals. Also disclosed are novel amines and intermediates used in the preparation of the naphthyridine- and quinoline-carboxylic acids.

16 Claims, No Drawings

1-TERTIARY-ALKYL-SUBSTITUTED NAPHTHYRIDINE CARBOXYLIC ACID ANTIBACTERIAL AGENTS

CROSS-REFERENCE

This application is a continuation of co-pending application Ser. No. 099,231 filed Sept. 25, 1987 now abandoned which is a continuation-in-part of Ser. No. 916,752 filed Oct. 8, 1986 and now abandoned.

BACKGROUND OF THE INVENTION

1. Field of the Invention

This invention relates to novel 4-oxo-naphthyridine- and 4-oxo-quinoline-3-carboxylic acids derivatives having anti-bacterial activity, to compositions containing the same, and to novel amines and intermediates used in the preparation of the same.

2. Description of the Prior Art

R. Albrecht, *Progress in Drug Research*, 21, 9–104(1977), describes the development of numerous structural variants having antibacterial activity which are based on the structure of nalidixic acid (1-ethyl-1,4-dihydro-7-methyl-4-oxo-1,8-naphthyridine-3-carboxylic acid) having the following structural formula:

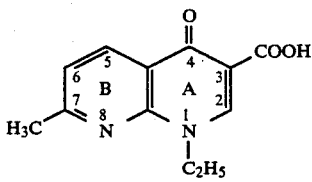

One such variant described by Albrecht is the class of compounds referred to as quinoline derivatives, more particularly, derivatives of 1,4-dihydro-4-oxo-3-quinolinecarboxylic acids having the following structural formula:

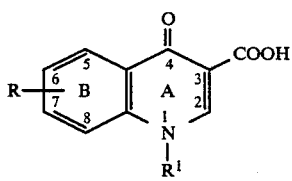

Such quinolones unsubstituted in the benzene nucleus, B, wherein R is H, are described as having only slight antibacterial activity. There are disclosed numerous quinoline derivatives having the above structural formula wherein the benzene nucleus, B, possesses substituents selected from halogen, alkyl, cycloalkyl, unsubstituted and substituted phenyl and pyridyl, piperidinyl and piperazinyl to name but a few, especially when such substituent is in the 7-position. See pages 12–15.

Further, there are disclosed numerous quinoline derivatives having the above structural formula wherein the pyridone nucleus, A, possesses various substituents in the 1-position selected from unsubstituted lower alkyl groups or lower alkyl substituted with, for example, halogen and hydroxy-groups, lower alkenyl, alkynyl, and unsubstituted and substituted phenyl. Particularly, it is disclosed that in a comparison of activity of these quinoline derivatives having an alkyl group in the 1-position, the effects achieved with smaller radicals always proved to be best and, further, that as a rule the best activity is obtained with the ethyl group. See page 25, lines 1–5.

Another variant described by Albrecht is the class of compounds referred to as naphthyridine derivatives, i.e. 1,8-naphthyridine or more particularly 1,4-dihydro-4-oxo-1,8-naphthyridine-3-carboxylic acid derivatives, having the following structural formula:

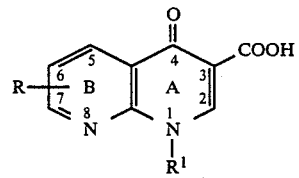

Among the 1,8-naphthyridine derivatives having the above structural formula, there are disclosed derivatives having piperazinyl and pyrrolidinyl groups in the 7-position and ethyl in the 1-position. See pages 51–56. As regards substituents in the 1-position, it is disclosed that among those same 1-position substituents described above in the quinoline derivatives, maximum activity is achieved with ethyl or propyl groups whereas all smaller or larger alkyl groups or those with additional double bonds or functional groups decrease activity. See page 60, lines 8–19.

M. P. Wentland and J. B. Cornett, *Annual Reports In Medicinal Chemistry*, 20, 145–154 (1985) describe modifications and developments in the area of quinolone antibacterial agents subsequent to the review of Albrecht above, particularly with emphasis on developments in 6-fluoro-7-piperazinylquinolones directed toward increasing antibacterial activity against Gram-positive bacteria and against anaerobes as well as against Gram-negative bacteria in comparison to the activity demonstrated by nalidixic acid. Among the more recent agents disclosed are the agents referred to as norfloxacin (1-ethyl-6-fluoro-1,4-dihydro-7-(1-piperazinyl)-4-oxo-quinoline-3-carboxylic acid) and ciprofloxacin (1-cyclopropyl-6-fluoro-1,4-dihydro-7-(1-piperazinyl)-4-oxo-quinoline-3-carboxylic acid).

U.S. Pat. No. 3,590,036 discloses numerous 1-substituted-1,4-dihydro-4-oxo-1,8-naphthyridine-3-carboxylic acids and derivatives thereof having the following formula, including nalidixic acid mentioned above, wherein the substituent on the 1-position can be aliphatic hydrocarbon radicals having one to ten carbon atoms inclusive such as, for example, alkyl, alkenyl and alkynyl radicals. Illustrative of these radicals are methyl, ethyl, n-propyl, i-propyl, 2-butyl, isoamyl, and the like, when alkyl; and 2-propenyl (allyl), 2-methyl-2-propenyl, 3-butenyl, and the like when alkenyl. The substituents on the pyridine nucleus, that is at the 5-, 6-, and 7-positions of the naphthyridine ring system, can be lower-alkyl, halo, and lower-cycloalkylamino.

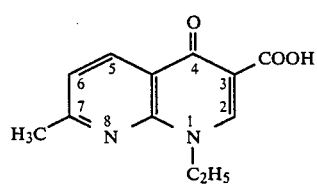

U.S. Pat. No. 4,284,629 discloses the preparation of certain 4-pyridone-3-carboxylic acids and derivatives thereof having the following structural formula:

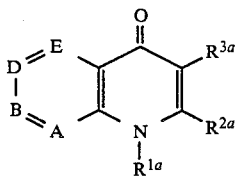

or a salt thereof wherein R$^{1a}$ denotes an alkyl, cycloalkyl, aralkyl, aryl or an amino group; R$^{2a}$ denotes a hydrogen atom or an alkyl, aralkyl or an aryl group; R$^{3a}$ denotes a derivative of a carboxyl group such as a nitrile or ester group; and up to three of the symbols A, B, D and E denote a nitrogen atom and the remaining of the symbols A, B, D, and E denote an optionally substituted carbon atom. Although the patent discloses that particularly preferred aliphatic radicals R$^{1a}$ are ethyl and tert-butyl, there is disclosed among the thirty-five actual examples a single example illustrating tertiary-butyl as the R$^{1a}$ radical, namely, 1-t-butyl-1,4-dihydro-7-methyl-4-oxo-1,8-naphthyridine-3-carboxylic acid (Example 25). However, no biological activity data is disclosed for this example.

U.S. Pat. Nos. 4,359,578 and 4,352,803 disclose antibacterial compounds having the following structural formula:

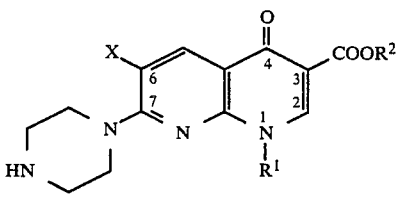

wherein X is a halogen atom, especially a fluorine atom, R$^1$ is an ethyl or vinyl group, and R$^2$ is a hydrogen atom or a lower alkyl group, and non-toxic salts thereof.

U.S. Pat. No. 4,146,719 discloses the compound, 1-ethyl-6-fluoro-1,4-dihydro-7-(1-piperazinyl)-4-oxoquinoline-3-carboxylic acid (norfloxacin) and the hydrates and addition salts thereof.

German Offen. DE 3142854 discloses 1-cyclopropyl-6-fluoro-1,4-dihydro-4-oxo-7-piperazinyl-quinoline-3-carboxylic acids including the specific compound wherein the substituent in the 7-position is unsubstituted piperazinyl (ciprofloxacin) as well as 4-substituted piperazinyl wherein the substituent is methyl, ethyl, or beta-hydroxyethyl.

EP 0,153,163 discloses antibacterial compounds having the following structural formula:

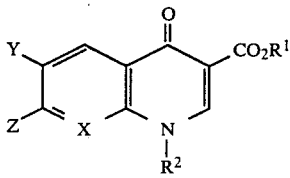

wherein X is CH, C—Cl, C—F, C—OH, C—O—alkyl having from one to three carbon atoms, C—NH—alkyl having from one to three carbon atoms or N; Y is H, F, Cl or Br; Z is representative of heterocyclic substituents having the formula

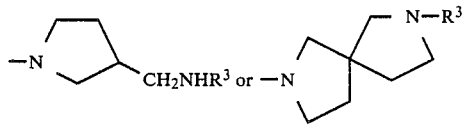

wherein R$^3$ is hydrogen, methyl, ethyl, 1- or 2-propyl; R$^1$ is hydrogen, alkyl having one to six carbon atoms or a cation; and R$^2$ is alkyl having one to four carbon atoms, vinyl, haloalkyl, or hydroxyalkyl having two to four carbon atoms, or cycloalkyl having three to six carbon atoms. Among the numerous actual examples there are disclosed the preparation of two compounds wherein R$^2$ is a tertiary alkyl group, namely, 1-methylcyclopropyl (See Examples 61 and 68). However, no data showing biological activity for these compounds is disclosed.

U.S. Pat. No. 4,571,396 (corresponding to EP 0,159,174) discloses certain naphthyridine- and quinoline-carboxylic acids having antibacterial activity and having the following structural formula:

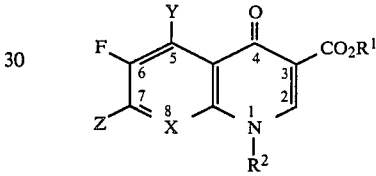

wherein Z is an amine substituent selected from

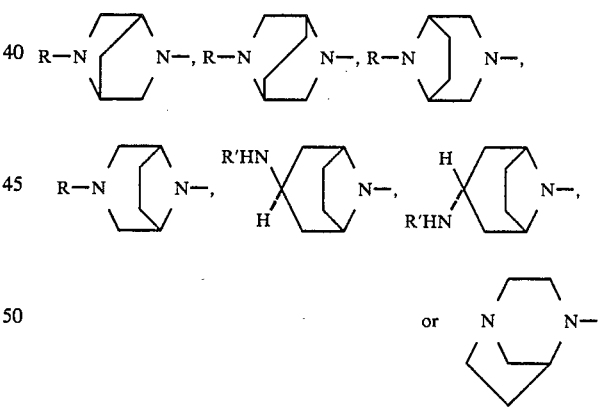

in which R is hydrogen, alkyl of one to three carbon atoms, hydroxyalkyl of two to three carbon atoms, benzyl or p-aminobenzyl; R' is hydrogen or alkanoyl of one to three carbon atoms; X is CH, CF, or N; Y is hydrogen, fluoro, or amino; R$^1$ is hydrogen, alkyl having from one to six carbon atoms or a cation; and R$^2$ is alkyl having one to four carbon atoms, vinyl, haloalkyl, or hydroxyalkyl having two to four carbon atoms, or cycloalkyl having three to six carbon atoms, and the pharmaceutically acceptable acid addition or base salts thereof.

U.S. Pat. No. 4,556,658 discloses antibacterial compounds having the following structural formula

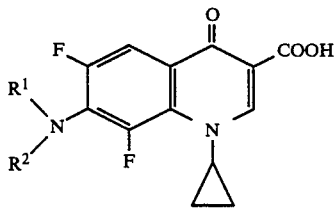

wherein $R^1$ and $R^2$ are identical or different and represent a $C_1$–$C_4$ alkyl radical which is optionally substituted by a hydroxyl, amino, methylamino or dimethylamino group, and $R^1$ and $R^2$ together with the nitrogen atom to which they are bonded, furthermore form a 5- or 6-membered heterocyclic ring which can additionally have, as a ring member, the atoms or groups —O—, —S—, —SO—, —SO$_2$— or >NR$^3$. The patented compounds are said to couple low toxicity with a broad antibacterial spectrum against Gram-positive and Gram-negative bacteria, in particular against Enterobacteriaceae, especially against those which are resistant to various antibiotics such as penicillins, cephalosporins, aminoglycosides, sulfonamides and the like.

U.S. Pat. No. 4,578,473 discloses an improved process to produce a compound having the structural formula

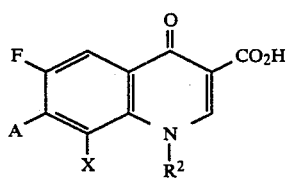

wherein A is a substituted amino group, $R^1R^2N$—; X is H or F; and $R^2$ is $C_1$–$C_3$ alkyl or $C_1$–$C_6$ cycloalkyl.

U.S. Pat. Nos. 4,559,341 and 4,559,342 disclose derivatives of the above-mentioned ciprofloxacin having the structural formula

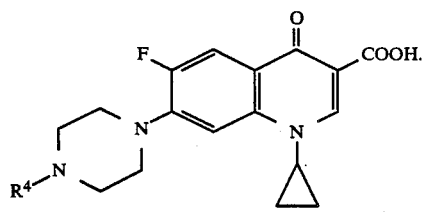

EP 0 166 939 discloses antibacterial 1-cyclopropyl-6-fluoro-1,4-dihydro-4-oxo-7-(3-oxo-1-piperazinyl)-3-quinolinecarboxylic acids having the structural formula

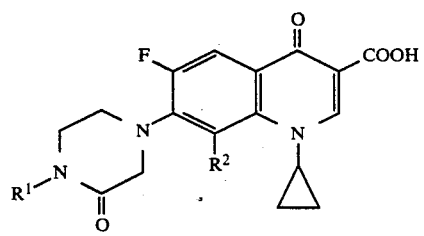

EP 0 167 763 discloses antibacterial compounds having the structural formula

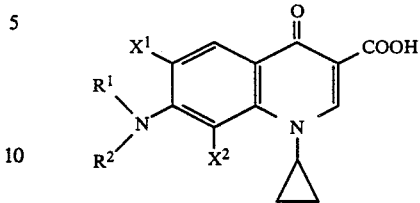

wherein $X^1$ and $X^2$ are the same or different and represent Cl or F provided that they are not both F at the same time and $R^1$ and $R^2$, together with the nitrogen atom to which they are bound, form a 5- or 6-membered ring which can further include —O—, —S—, —SO—, —SO$_2$—, >N—R$^3$ or —CONR$^3$.

Spanish Patent 8504767 discloses a process to produce compounds having the structural formula

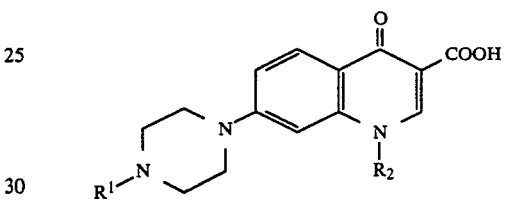

wherein $R_1$ is hydrogen or lower alkyl, for example, methyl, ethyl, or isopropyl, and $R_2$ is methyl or ethyl, by reacting a 3-chloro-4-fluoro-(N-alkyl)aniline with ethoxymethylenemalononitrile, cyclizing the resulting intermediate under Friedel-Crafts conditions, and reacting the resulting intermediate with an appropriate piperazine.

South African Patent Application Publication No. 853954 discloses antibacterial compounds having the structural formula

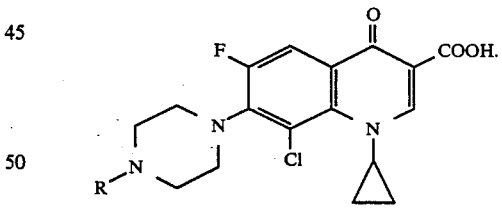

U.S. Pat. No. 4,563,448 discloses a method of combating plant-pathogenic bacteria using a cyclopropyl-1,4-dihydro-4-oxo-3-quinolinecarboxylic acid derivative of the formula

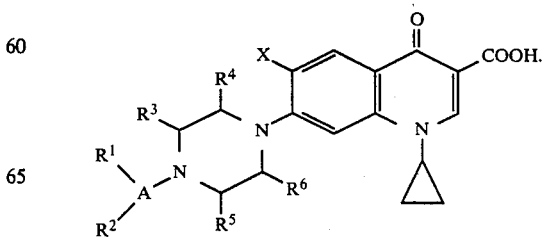

Great Britain Patent Application Publication 2 160 519 A discloses quinolone compounds having antibacterial activity having the structural formula

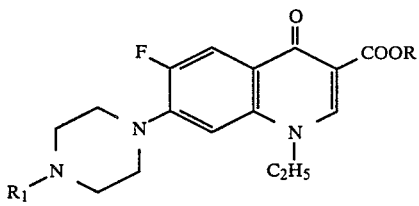

wherein R₁ is H or alkyl.

EP 0 132 845 discloses antibacterial 1,8-naphthyridine derivatives of the formula

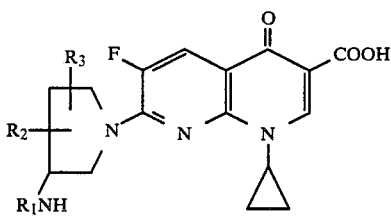

wherein R₁, R₂ and R₃ are the same or different and can be hydrogen or lower alkyl having 1 to 5 carbon atoms.

EP 0 134 165 discloses antibacterial 7-(pyrrol-1-yl) derivatives of 1-ethyl-1,4-dihydro-4-oxo-quinoline-3-carboxylic acid and 1-ethyl-1,4-dihydro-4-oxo-(1,8-naphthyridine)-3-carboxylic acid of the formula

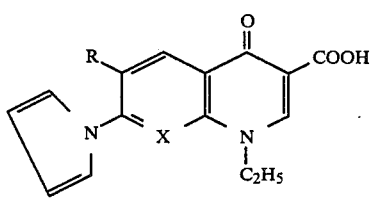

wherein X is a carbon atom or nitrogen atom and R is hydrogen or fluoro.

U.S. Pat. No. 4,341,784 discloses antibacterial 7-(3-amino-1-pyrrolidinyl)-1-ethyl-6-fluoro-1,4-dihydro-4-oxo-1,8-naphthyridine-3-carboxylic acids of the formula

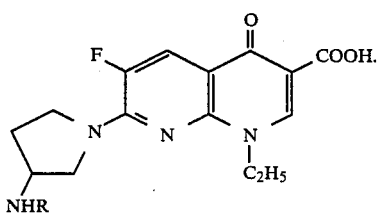

Although the recently developed compounds exhibit improvements in antibacterial activity, such as a broader activity spectrum, increased potency, improved absorbability, increased duration of action and improved stability, in comparison with previous compounds, there remains a need for compounds having an advantageous combination of these and other desirable properties.

These and other advantages as will be apparent to those skilled in the art to which this invention pertains are acheived by this invention which is described as follows.

SUMMARY OF THE INVENTION

This invention in a first aspect is a generic chemical compound representing one of the group of compounds consisting of naphthyridine- and quinoline-carboxylic acids and having the formula

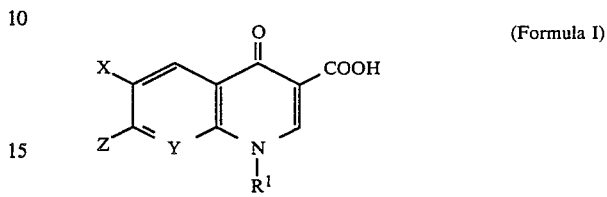

(Formula I)

in which $R^1$ is a unsubstituted or substituted tertiary-alkyl group wherein the t-alkyl group may contain 1-3 halo, e.g. fluoro, groups, X is a halogen or tirhalomethyl group, Y is a C or a N atom which provides a quinoline or a naphthyridine ring system, respectively, and Z is a N-heterocyclic ring selected from the group of piperazinyl, piperidinyl, 3-amino-1-pyrrolidinyl, 3-aminoalkyl-1-pyrrolidinyl, 2-aminoalkyl-morpholin-4-yl, 2-aminoalkyl-thiomorpholin-4-yl, and diazabicycloakyl groups containing 7-9 atoms in the diazobicycloalkyl ring system.

In another aspect, this invention is an intermediate for the preparation of compounds of Formula I having the generic formula

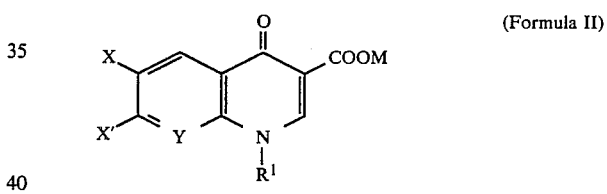

(Formula II)

wherein $R^1$, and X and Y are as defined above, X' may be the same as X above or an alkyl-, aryl- or aralkyl-sulfonyl and M is H or alkyl or a salt-forming metal cation or ammonium ion.

In yet another aspect, this invention is an amine compound, Z-H, useful in preparing compounds of Formula I.

DETAILED DESCRIPTION OF THE INVENTION

In one aspect, this invention is a compound having the formula

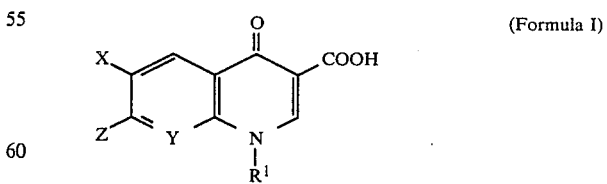

(Formula I)

wherein:

$R^1$ is a unsubstituted or substituted tertiary alkyl group selected from

—C(CH₃)₃, —C(CH₃)₂CH₂CH₃, —C(C₆H₅)(CH₃)₂,

-continued

—C(C₆H₅)CHRCH₂, —C(CH₃)CHRCH₂,

—C(CH₃)CH₂CH₂CH₂, —C(CH₃)=CH₂, and

[adamantyl structure]

wherein R is H or CH₃ and wherein the t-alkyl group may contain 1-3 halo, e.g. fluoro groups;
X is a member of the group of halogen groups selected from F, Cl and Br and trihaloalkyl groups selected from CF₃ and CCl₃;
Y is selected from CH, CF, CCl, CBr, and N; and
Z is selected from

[structure with A, B, C, D, R²—N, N—]

[structure with R²N—(CH₂)ₙ, A, B, C, D, N—]

[structure: W  N—, wherein W is NR², S or O, with R²₂N—(CH₂)ₙ]

R²—N(CH₂)ₙ N—,

R²—N(CH₂)ₙ N—,

R²—N(CH₂)ₙ N—, and

N—(CH₂)ₙ N— wherein R² is independently selected from H, unsubstituted and substituted alkyl having 1 to 6 carbon atoms wherein the substituent is independently selected from 1-3 hydroxy, fluoro, chloro, amino, alkylamino, trifluoroacetylamino, and phenyl groups; cycloalkyl having 3 to 6 carbon atoms; and cycloalkenyl having 3 to 6 carbon atoms; and wherein A, B, C, and D are independently selected from H; unsubstituted and substituted lower alkyl having 1 to 4 carbon atoms wherein the substituent is independently selected from 1-3 hydroxy, fluoro, chloro, amino, alkylamino, trifluoroacetylamino, and phenyl groups; and wherein n, when present, is selected from the integers 0, 1, 2, and 3;
provided that when R¹ is

—C(CH₃)CHRCH₂ then Z is not

R²HN(CH₂)ₙ—[pyrrolidine]—N—, and pharmaceutically acceptable acid addition and base salts thereof.

In those embodiments above containing the R²₂N— moeity wherein each of the R² groups is other than H, then R² is independently selected from CH₃ and C₂H₅.

It is to be understood that the formulas herein representing the various compounds according to the invention are intended to embrace all optical isomers within the scope of the given formulas unless otherwise indicated.

In another aspect, as is mentioned above, this invention is a pharmaceutical composition comprising an antibacterially effective amount of a compound of Formula I above.

In still another aspect, this invention is a method of combatting bacterial infection in warm-blooded animals comprising administering to said animals an antibacterially effective amount of a compound of Formula I or of a pharmaceutical composition thereof.

In yet another aspect, this invention is a compound having the formula (Formula II)

[naphthyridine structure with X, X', Y, N-R¹, COOM, O]

wherein:
R¹ is a tertiary alkyl group selected from

—C(CH₃)₃, —C(CH₃)₂CH₂CH₃, —C(C₆H₅)(CH₃)₂,

—C(C₆H₅)CHRCH₂, —C(CH₃)CHRCH₂,

—C(CH₃)CH₂CH₂CH₂, —C(CH₃)=CH₂, and

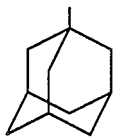

wherein R is H or CH₃;

X is a member of the group of halogen groups selected from F, Cl, and Br and trihaloalkyl groups selected from CF₃ and CCl₃;

X' may be the same as X or an alkyl-, aryl- or aralkyl-sulfonyl;

Y is selected from CH, CF, CCl, CBr and N; and

M is selected from H, C₁–C₄ alkyl and alkali and alkaline earth metal ions, and ammonium ions.

In still another aspect, this invention is a compound represented by the formula Z—H    (Formula III)

wherein ZH is selected from

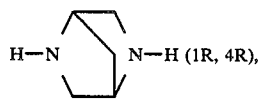

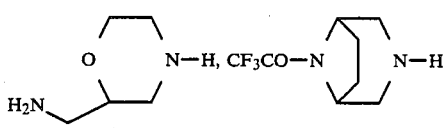

and the free amine hydrolysis product thereof, and

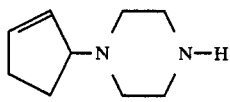

Preferred compounds of Formula I above according to this invention are those wherein R¹ is unsubstituted or substituted

—C(CH₃)₃, —C(CH₃)₂CH₂CH₂CH₃, —C(CH₃)CH₂CH₂,

—C(CH₃)CH₂CH₂CH₂ and —C(CH₃)=CH₂;

X is F;
Y is selected from CH, CF and N; and
Z is selected from

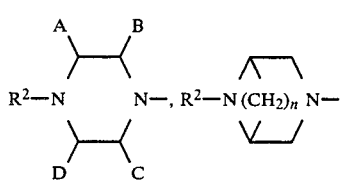

wherein R² is independently selected from H, CH₃, —C₂H₅ and —C(CH₃)₃ and

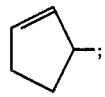

A, B, C, and D are independently selected from H, CH₃ and C₂H₅; and n is selected from 0, 1, and 2.

More preferred compounds of Formula I above according to this invention are those wherein R¹ is —C(CH₃)₃, —C(CH₂F)(CH₃)₂, —C(CH₂F)₂CH₃, or —C(CF₃)(CH₃)₂;
X is F;
Y is selected from CH and N; and
Z is selected from

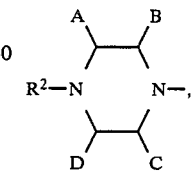

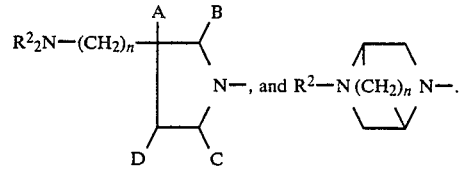

Especially preferred compounds of Formula I according to this invention are those wherein R¹ is —C(CH₃)₃;
X is F;
Y is CH; and
Z is selected from

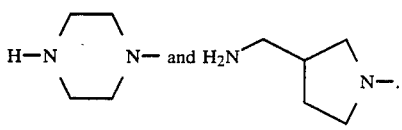

Further especially preferred compounds of Formula I according to this invention are those wherein R¹ is —C(CH₃)₃;
X is F;
Y is N; and
Z is selected from

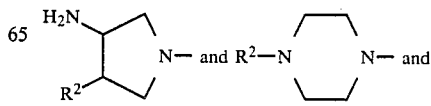

-continued

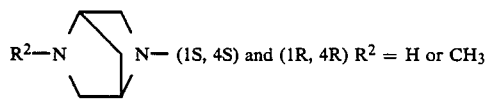

Most especially preferred are the compound of Formula I wherein $R^1$ is $-C(CH_3)_3$, X is F, Y is N and Z is selected from

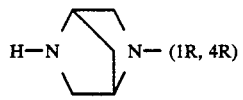

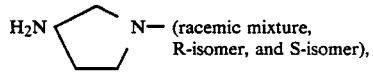

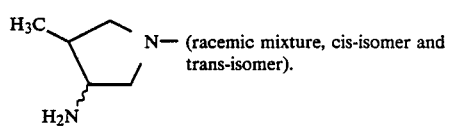

By the expressions "cis-isomer" and "trans-isomer" above is meant that the methyl and amino groups are on the same side of the plane of the pyrrolidine ring system or are on opposite sides of the plane of the pyrrolidine ring system, respectively. It will be apparent to those skilled in the art that here there are present 2 asymmetric carbon atoms and, thus, there are two isomers when the methyl and amino groups are cis and two isomers when they are trans.

The compounds having formulas I, II, and III may contain an asymmetric carbon atom. As is mentioned above, the formulas I, II and III herein representing the various compounds of the invention are intended to embrace all optical isomers, as well as racemic mixtures thereof, of the compounds within the scope of the given formula.

The compounds of this invention may be readily prepared by reacting a compound having the formula

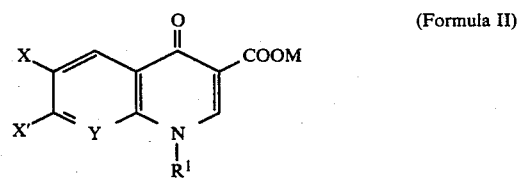

(Formula II)

wherein $R^1$, X, X', Y, and M are as defined above, with an amine,

for example, an amine corresponding to the formula

Z—H           (Formula III)

wherein Z is also as defined above.

Although X' in Formula II above may be selected from the same substituents, namely, F, Cl and Br and $CF_3$ and $CCl_3$, which define "X", X' also may be an organic leaving group other than $CF_3$ and $CCl_3$. More preferably, X' may be selected from F and Cl and an organic leaving group such as alkylsulfonyl (for example methanesulfonyl), arylsulfonyl (for example phenylsulfonyl), and aralkylsulfonyl (for example p-toluenesulfonyl).

The intermediates of Formula II, wherein $R^1$ is a tertiary alkyl group as defined above, are novel but may be prepared from known starting materials by standard, or conventional, procedures or by variations thereof. Representative of such procedures are those disclosed in U.S. Pat. No. 4,571,396 and others of the references disclosed in the Description of the Prior Art above.

Certain of the amine starting materials represented by the formula Z—H (Formula III) are novel and may be prepared as described below.

The following reaction sequence illustrates a typical preparation of the compounds of formulas I and also II. In the reaction sequence, R=Et or $PhCH_2$, $X=X^1=F$ or Cl, and Y=CH, CF or N. According to this method polyhalogenated aromatic acid (1) is converted with sulfuryl chloride to acid chloride (2) which acylates malonate diester in the presence of magnesium ethylate to give the aroylmalonate (3).

Partial hydrolysis and decarboxylation of (3) in aqueous medium using catalytic amounts of p-toluene sulfonic acid give (4) which is treated with triethyl orthoformate and acetic anhydride to give (5). Reaction of (5) with t-butylamine in ethyl alcohol leads to an isomeric mixture of (6) which is cyclised to (7) with a slight excess of sodium hydride in dioxane. Compound (10) may be obtained from (7) by two ways: (a) Ester (7) is first hydrolyzed under basic condition to lead to carboxylic acid (8) which reacts with the appropriate amine to give (10); and (b) Ester (7) can be converted to (9) with the appropriate amine and the ester (9) hydrolyzed under basic condition to (10).

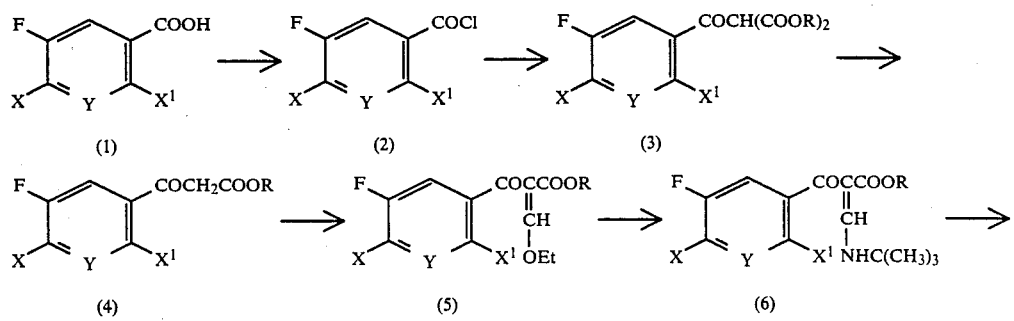

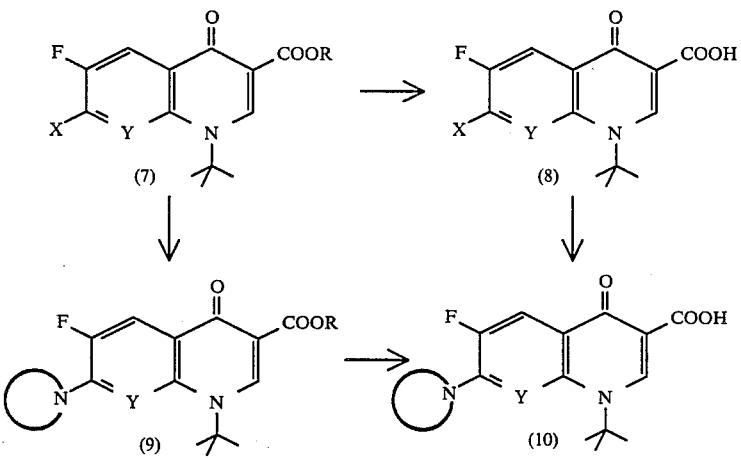

Preferred species of the compounds of this invention include the following:

1-(1,1-dimethylethyl)-1,4-dihydro-6-fluoro-7-piperazinyl-4-oxo-3-quinolinecarboxylic acid, methane sulfonate.

7-[4-(cyclopenten-3-yl)-1-piperazinyl]-1-(1,1-dimethylethyl)-1,4-dihydro-6-fluoro-4-oxo-3-quinolinecarboxylic acid, hydrochloride.

7-(8-methyl-3,8-diazabicyclo[3.2.1]octan-3-yl)-1-(1,1-dimethylethyl)-1,4-dihydro-6-fluoro-4-oxo-3-quinolinecarboxylic acid, hydrochloride.

7-[(3-phenyl)-1-piperazinyl]-1-(1,1-dimethylethyl)-1,4-dihydro-6-fluoro-4-oxo-3-quinolinecarboxylic acid, methanesulfonate.

1-(1,1-dimethylethyl)-1,4-dihydro-6-fluoro-7-(4-methyl-piperazinyl)-4-oxo-3-quinolinecarboxylic acid, hydrochloride.

7-(2,5-diazabicyclo[2.2.2]octan-2-yl)-1-(1,1-dimethylethyl)-1,4-dihydro-6-fluoro-4-oxo-3-quinolinecarboxylic acid.

7-(1S,4S-2,5-diazabicyclo[2.2.1]heptan-2-yl)-1-(1,1-dimethylethyl)-1,4-dihydro-6-fluoro-4-oxo-3-quinolinecarboxylic acid.

7-(3-(aminomethyl)-1-pyrrolidinyl)-1-(1,1-dimethylethyl)-1,4-dihydro-6-fluoro-4-oxo-3-quinolinecarboxylic acid.

7-(3-(ethylamino)methyl-1-pyrrolidinyl)-1-(1,1-dimethylethyl)-1,4-dihydro-6-fluoro-4-oxo-3-quinolinecarboxylic acid.

7-(3-methyl-1-piperazinyl)-1-(1,1-dimethylethyl)-1,4-dihydro-6-fluoro-4-oxo-3-quinolinecarboxylic acid.

7-((3,5-dimethyl)-1-piperazinyl)-1-(1,1-dimethylethyl)-1,4-dihydro-6-fluoro-4-oxo-3-quinolinecarboxylic acid.

7-(4-(dimethylamino)-1-piperazinyl)-1-(1,1-dimethylethyl)-1,4-dihydro-6-fluoro-4-oxo-3-quinolinecarboxylic acid.

7-(4-(1,1-dimethylethyl)-1-piperazinyl)-1-(1,1-dimethylethyl)-1,4-dihydro-6-fluoro-4-oxo-3-quinolinecarboxylic acid.

7-piperazinyl-1-(1,1-dimethylethyl)-1,4-dihydro-6,8-difluoro-4-oxo-3-quinolinecarboxylic acid.

7-(3-(ethylamino)methyl-1-pyrrolidinyl)-1-(1,1-dimethylethyl)-1,4-dihydro-6,8-difluoro-4-oxo-3-quinolinecarboxylic acid.

7-(3-amino-1-pyrrolidinyl)-1-(1,1-dimethylethyl)-1,4-dihydro-6-fluoro-4-oxo-3-quinolinecarboxylic acid, hydrochloride 7-piperazinyl-1-(1,1-dimethylethyl)-1,4-dihydro-6-fluoro-4-oxo-1,8-naphthyridine-3-carboxylic acid.

7-(3-methyl-1-piperazinyl)-1-(1,1-dimethylethyl)-1,4-dihydro-6-fluoro-4-oxo-1,8-naphthyridine-3-carboxylic acid.

7-(1S,4S-2,5-diazabicyclo[2.2.1]heptan-2-yl)-1-(1,1-dimethylethyl)-1,4-dihydro-6-fluoro-4-oxo-1,8-naphthyridine-3-carboxylic acid.

7-(2,5-diazabicyclo[2.2.2]octan-2-yl)-1-(1,1-dimethylethyl)-1,4-dihydro-6-fluoro-4-oxo-1,8-naphthyridine-3-carboxylic acid.

7-(4-(cyclopenten-3-yl)-1-piperazinyl)-1-(1,1-dimethylethyl)-1,4-dihydro-6-fluoro-4-oxo-1,8-naphthyridine-3-carboxylic acid.

7-(3-(aminomethyl)-1-pyrrolidinyl)-1-(1,1-dimethylethyl)-1,4-dihydro-6-fluoro-4-oxo-1,8-naphthyridine-3-carboxylic acid.

7-(3-((ethylamino)methyl)-1-pyrrolidinyl)-1-(1,1-dimethylethyl)-1,4-dihydro-6-fluoro-4-oxo-1,8-naphthyridine-3-carboxylic acid.

7-(3-methyl-1-piperazinyl)-1-(1,1-dimethylethyl)-1,4-dihydro-6-fluoro-4-oxo-1,8-naphthyridine-3-carboxylic acid.

7-(3,4-dimethyl-1-piperazinyl)-1-(1,1-dimethylethyl)-1,4-dihydro-6-fluoro-4-oxo-1,8-naphthyridine-3-carboxylic acid.

7-(3-phenyl-1-piperazinyl)-1-(1,1-dimethylethyl)-1,4-dihydro-6-fluoro-4-oxo-1,8-naphthyridine-3-carboxylic acid, methanesulfonate.

7-(1R,4R-2,5-diazabicyclo[2.2.1]heptan-2-yl)-1-(1,1-dimethylethyl)-1,4-dihydro-6-fluoro-4-oxo-1,8-naphthyridine-3-carboxylic acid.

7-(8-methyl-3,8-diazabicyclo[3.2.1]octan-3-yl)-1-(1,1-dimethylethyl)-1,4-dihydro-6-fluoro-4-oxo-1,8-naphthyridine-3-carboxylic acid, methanesulfonate salt.

7-(3,8-diazabicyclo[3.2.1]octan-3-yl)-1-(1,1-dimethylethyl)-1,4-dihydro-6-fluoro-4-oxo-1,8-naphthyridine-3-carboxylic acid, methanesulfonate.

7-(2-aminomethyl-morpholin-4-yl)-1-(1,1-dimethylethyl)-1,4-dihydro-6-fluoro-4-oxo-1,8-naphthyridine-3-carboxylic acid.

7-(3-amino-1-pyrrolidinyl)-1-(1,1-dimethylethyl)-1,4-dihydro-6-fluoro-4-oxo-1,8-naphthyridine-3-carboxylic acid.

7-[(S)-3-amino-1-pyrrolidinyl]-1-(1,1-dimethylethyl)-6-fluoro-1,4-dihydro-4-oxo-1,8-naphthyridine-3-carboxylic acid.

7-(3-amino-4-methyl-pyrrolidin-1-yl)-1-(1,1-dimethylethyl)-1,4-dihydro-6-fluoro-4-oxo-1,8-naphthyridine-3-carboxylic acid.

7-(trans-3-amino-4-methyl-pyrrolidin-1-yl)-1-(1,1-dimethylethyl)-1,4-dihydro-6-fluoro-4-oxo-1,8-naphthyridine-3-carboxylic acid.

7-(cis-3-amino-4-methyl-pyrrolidin-1-yl)-1-(1,1-dimethylethyl)-1,4-dihydro-6-fluoro-4-oxo-1,8-naphthyridine-3-carboxylic acid.

The compounds of Formula I according to this invention may be provided as pharmaceutically acceptable acid addition and base salts wherein the anion or cation, respectively, does not contribute significantly to the toxicity of the salt and which salts are compatible with the standard and conventional pharmaceutically acceptable carriers and other conventional adjuvants and excipients customarily employed in producing pharmaceutical compositions adapted for oral or parenteral administration. The acid addition salts are formed by conventional techniques involving reaction of compounds of Formula I with mineral acids such as, for example, hydrochloric acid, hydrobromic acid, phosphoric acid, and sulfuric acid, and with organic carboxylic and sulfonic acids such as, for example, acetic acid, citric acid, maleic acid, succinic acid, benzoic acid, tartaric acid, ascorbic acid, methanesulfonic acid, ethanesulfonic acid, 2-hydroxyethanesulfonic acid, p-toluenesulfonic acid, and the like.

Pharmaceutically acceptable base salts are formed by conventional techniques involving reaction of the compounds of Formula I with alkali (Na, K) and alkaline earth (Ca, Ba, Zn, Mn) metal bases, more preferably with alkali metal bases such as, for example, dilute solutions of sodium hydroxide, and potassium carbonate. Also, pharmaceutically acceptable base salts are formed by conventional techniques involving reaction with amines such as, for example, triethylamine, dibenzylamine, triethanolamine, ethanolamine, N,N'-dibenzylethylenediamine, procaine and equivalent amines.

The pharmaceutical compositions of this invention may be prepared by combining the compounds of Formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound, and the desired concentration. Generally, the quantity of active component will range between 0.5% to about 90% by weight of the composition.

In therapeutic use for treating, or combatting bacterial infections in warm-blooded animals, the compounds or pharmaceutical compositions thereof will be administered at a dosage to obtain and maintain a concentration that is, an amount, or blood-level of active component in the animal undergoing treatment which will be antibacterially effective. Generally, such antibacterially effective amount of dosage of active component will be in the range of about 0.1 to about 15, more preferably about 1.5 to about 10, still more preferably about 3 to about 7 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation.

The compounds of formula I according to this invention are advantageously administered parenterally, i.e. by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5-6. Suitable buffering agents include, for example, trisodium orthophosphate, sodium bicarbonate, sodium citrate, N-methylglucamine, L(+)-lysine and L(+)-arginine to name but a few representative buffering agents. The compound according to formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage in the range of about 0.1 to about 15, more preferably about 1.5 to about 10, still more preferably about 3 to about 7 mg/kg of body weight/day.

The following examples are presented to illustrate but a few representative embodiments of the invention and are not to be construed as limiting in scope. All parts and percentages are by weight and all temperatures are in degrees Celsius unless otherwise indicated.

Examples 1 to 44 describe different methods used to prepare representative compounds according to the invention.

Examples A to H describe preparations of sofar unknown amines.

Examples I to XII describe preparations of quinolone and naphthyridone intermediates bearing the t-butyl (1,1-dimethylethyl) group.

PREPARATION OF QUINOLONE AND NAPHTHYRIDONE ANTIBACTERIAL COMPOUNDS

EXAMPLE 1

1-(1,1-DIMETHYLETHYL)-1,4-DIHYDRO-6-FLUORO-7-PIPERAZINYL-4-OXO-3-QUINOLINECARBOXYLIC ACID, METHANESULFONATE

Method 1:

A suspension of 17.7 g (59.4 mmoles) 1-(1,1-dimethylethyl)-1,4-dihydro-6-fluoro-7-chloro-4-oxo-3-quinolinecarboxylic acid and 20.49 g (238 mmoles) of piperazine in 53 mL pyridine was heated at 100° C. for 18 hours under nitrogen. The suspension was cooled at +5° C., the precipitate was filtered and washed with 5 mL pyridine and cold ether. The precipitate was taken up in 110 mL water and the pH adjusted to 7.2 with 6N hydrochloric acid. The precipitate was filtered and washed with cold water to give 14.16 g of crude product. The crude product was suspended in 823 mL 95% aqueous isopropanol. The suspension was heated to reflux and 3.20 mL (49.3 mmoles) of methanesulfonic acid was added. The mixture was kept at room temperature overnight, filtered and dried to yield 8.12 g of titled compound. mp>270° C.

Method 2

A mixture of 0.3 g (1.01 mmole) 1-(1,1-dimethylethyl)-6-fluoro-7-chloro-1,4-dihydro-4-oxo-3-quinolinecarboxylic acid and 0.3 g (3.48 mmoles) piperazine in 1 mL pyridine was heated under reflux for 18 hours. After cooling the mixture was concentrated under reduced pressure. The residue was poured in 10 mL of 10% acetic acid. After filtration of little insoluble the solution was taken to pH 6.5, saturated with brine and extracted three times with dichloromethane. After evaporation the resulting solid obtained was purified in water to give 0.15 g of 1-(1,1-dimethylethyl)-1,4-dihydro-6-fluoro-7-piperazinyl-4-oxo-3-quinolinecarboxylic acid purified as in method 1.

The following compounds were also prepared by following substantially the above procedure:

EXAMPLE 2

7-[4-(CYCLOPENTEN-3-YL)-1-PIPERAZINYL]-1-(1,1-DIMETHYLETHYL)1,4-DIHYDRO-6-FLUORO-4-OXO-3-QUINOLINECARBOXYLIC ACID, HYDROCHLORIDE

EXAMPLE 3

7-(8-METHYL-3,8-DIAZABICYCLO[3.2.1]OCTAN-3-YL)-1-(1,1-DIMETHYLETHYL)-1,4-DIHYDRO-6-FLUORO-4-OXO-3-QUINOLINECARBOXYLIC ACID, HYDROCHLORIDE. MP 308° C.

EXAMPLE 4

7-[(3-PHENYL)-1-PIPERAZINYL]-1-(1,1-DIMETHYLETHYL)-1,4-DIHYDRO-6-FLUORO-4-OXO-3-QUINOLINECARBOXYLIC ACID, METHANESULFONATE. MP>300° C.

EXAMPLE 5

7-(3-AMINO-3-METHYL-PYRROLIDIN-1-YL)-1-(1,1-DIMETHYLETHYL)-1,4-DIHYDRO-4-OXO-6-FLUORO-3-QUINOLINECARBOXYLIC ACID. MP>260° C.

EXAMPLE 6

1-(1,1-DIMETHYLETHYL)-1,4-DIHYDRO-6-FLUORO-7-(4-METHYL-1-PIPERAZINYL)-4-OXO-3-QUINOLINECARBOXYLIC ACID, HYDROCHLORIDE

A mixture of 1.4 g (4.7 mmoles) 1-(1,1-dimethylethyl)-1,4-dihydro-6,7-difluoro-4-oxo-3-quinolinecarboxylic acid and 2.08 mL (18.8 mmoles) N-methylpiperazine were heated at 100° C. under nitrogen for 18 hours. The mixture was evaporated to dryness under reduced pressure. The residue was dissolved in water and the solution was adjusted to pH 6.5–7.0 with 5N hydrochloric acid. The precipitate was filtered and washed two times with water and once with ethanol to give 0.63 g crude material, which was recrystallized as its hydrochloride in ethanol to give 0.54 g of the titled compound. MP>270° C.

The following compounds were also prepared by following substantially the above procedure:

EXAMPLE 7

7-(2,5-DIAZABICYCLO[2.2.2]OCTAN-2-YL)-1-(1,1-DIMETHYLETHYL)-1,4-DIHYDRO-6-FLUORO-4-OXO-3-QUINOLINECARBOXYLIC ACID. MP 164° C.

EXAMPLE 8

7-(1S,4S-2,5-DIAZABICYCLO[2.2.1]HEPTAN-2-YL)-1-(1,1-DIMETHYL)-1,4-DIHYDRO-6-FLUORO-4-OXO-3-QUINOLINECARBOXYLIC ACID. MP 243° C. $[\alpha]^D = -188°$ (C=0.25, 0.1N HCL).

EXAMPLE 9

7-(3-(AMINOMETHYL)-1-PYRROLIDINYL)-1-(1,1-DIMETHYLETHYL)-1,4-DIHYDRO-6-FLUORO-4-OXO-3-QUINOLINECARBOXYLIC ACID. MP 231° C.

EXAMPLE 10

7-(3-(ETHYLAMINO)METHYL-1-PYRROLIDINYL)-1-(1,1-DIMETHYLETHYL)-1,4-DIHYDRO-6-FLUORO-4-OXO-3-QUINOLINECARBOXYLIC ACID

EXAMPLE 11

7-(3-METHYL-1-PIPERAZINYL)-1-(1,1-DIMETHYLETHYL)-1,4-DIHYDRO-6-FLUORO-4-OXO-3-QUINOLINECARBOXYLIC ACID

EXAMPLE 12

7-((3,5-DIMETHYL)-1-PIPERAZINYL)-(1,1-DIMETHYLETHYL)-1,4-DIHYDRO-6-FLUORO-4-OXO-3-QUINOLINECARBOXYLIC ACID. MP 197° C.

EXAMPLE 13

7-(4-(DIMETHYLAMINO)-1-PIPERAZINYL)-1-(1,1-DIMETHYLETHYL)-1,4-DIHYDRO-6-FLUORO-4-OXO-3-QUINOLINECARBOXYLIC ACID. MP 226° C.

EXAMPLE 14

7-(1R,4R-2,5-DIAZABICYCLO[2.2.1]HEPTAN-2-yl)-1-(1,1-DIMETHYLETHYL)-1,4-DIHYDRO-6-FLUORO-4-OXO-3-QUINOLINECARBOXYLIC

ACID. MP 250° C. [α]$^D$=+172° (C=0.25% 0.1N HCl).

EXAMPLE 15

7-(4-(1,1-DIMETHYLETHYL)-1-PIPERAZINYL)-1-(1,1-DIMETHYLETHYL)-1,4-DIHYDRO-6-FLUORO-4-OXO-3-QUINOLINECARBOXYLIC ACID

A mixture of 0.45 g (1.51 mmoles) 1-(1,1-dimethylethyl)-1,4-dihydro-7-chloro-6-fluoro-4-oxo-3-quinolinecarboxylic acid and 0.65 g (4,56 mmoles) 1-(1,1-dimethylethyl)piperazine in 2 mL N-methylpyrrolidone were heated 5 hours at 100° C. The solvent was evaporated under reduced pressure. The residue was tritured in water. The precipitate was recrystallized in ethanol to give 0.136 g of titled compound. MP>270° C.

EXAMPLE 16

7-PIPERAZINYL-1-(1,1-DIMETHYLETHYL)-1,4-DIHYDRO-6,8-DIFLUORO-4-OXO-3-QUINOLINECARBOXYLIC ACID

To a refluxing solution of 0.87 g (10 mmoles) piperazine in 15 mL acetonitrile was added portionwise 1,10 g(3,36 mmoles) of 1-(1,1-dimethylethyl)-1,4-dihydro-6,7,8-trifluoro-4-oxo-3-quinoline carboxylic acid ethyl ester in 15 minutes. The mixture was refluxed 7 hours, cooled and evaporated to dryness. The residue was worked up with dichloromethane and brine to give 0.89 g of crystalline product which was used without further purification.

0.805 g (2,04 mmoles) of 7-piperazinyl-1-(1,1 dimethylethyl)-1,4-dihydro-6,8-difluoro-4-oxo-3-quinolinecarboxylic acid ethyl ester was hydrolyzed with 1,05 mL 2N NaOH for two hours. The solution was evaporated to dryness neutralized with 5% acetic acid (pH 7.0). The solid was filtered to give 0.585 g of titled compound.

The following compounds were also prepared by following substantially the above procedure.

EXAMPLE 17

7-(3-(ETHYLAMINO)METHYL-1-PYRROLIDINYL)-1-(1,1-DIMETHYLETHYL)-1,4-DIHYDRO-6,8-DIFLUORO-4-OXO-3-QUINOLINECARBOXYLIC ACID

EXAMPLE 18

7-(1R,4R-2,5-DIAZABICYCLO[2.2.1]HEPTAN-2-YL)-1-(1,1-DIMETHYLETHYL)-1,4-DIHYDRO-6,8-DIFLUORO-4-OXO-3-QUINOLINECARBOXYLIC ACID. MP>260° C.

EXAMPLE 19

7-(3-AMINO-1-PYRROLIDINYL)-1-(1,1-DIMETHYLETHYL)-1,4-DIHYDRO-6-FLUORO-4-OXO-3-QUINOLINECARBOXYLIC ACID, HYDROCHLORIDE

A mixture of 600 mg (2.13 mmoles) 1-(1,1-dimethylethyl)-1,4-dihydro-6,7-difluoro-4-oxo-3-quinolinecarboxylic acid, 700 mg (3.2 mmoles) of 3-trifluoroacetylamino pyrrolidine hydrochloride and 1.3 mL (8.5 mmoles) of 1,8-diazabicyclo[5.4.0]undec-7-ene in 3 mL pyridine was stirred 30 minutes at room temperature, evaporated to dryness and poured into water. The pH was adjusted to 7.5 with 1N hydrochloric acid. The precipitate was filtered to give 430 mg of 7-(3-trifluoroacetylamino-1-pyrrolidinyl)-1-(1,1-dimethylethyl)-1,4-dihydro-6-fluoro-4-oxo-3-quinolinecarboxylic acid. mp 200° C. dec. 409 mg (0.92 mmole) of that compound was suspended in 2 mL 1N NaOH and refluxed 2 hours. The solution was cooled and diluted with water, the pH was adjusted to 7.5 with 10% acetic acid. The precipitate was filtered, washed with water, dried and recrystallized as an hydrochloride in ethanol to give 180 mg of titled compound. MP>270° C.

EXAMPLE 20

7-PIPERAZINYL-1-(1,1-DIMETHYLETHYL)-1,4-DIHYDRO-6-FLUORO-4-OXO-1,8-NAPHTHYRIDINE-3-CARBOXYLIC ACID

To a refluxed solution of 487 mg (5.65 mmoles) piperazine in 30 mL acetonitrile was gradually added 612 mg (1.87 mmole) of 1-(1,1-dimethylethyl)-1,4-dihydro-6-fluoro-7-chloro-4-oxo-1,8-naphthyridine-3-carboxylic acid ethyl ester over a 10 mn period. The solution was refluxed 30 minutes and evaporated to dryness. The residue was taken up in water and filtered to give 435 mg of 7-piperazinyl-1-(1,1-dimethylethyl)-1,4-dihydro-6-fluoro-4-oxo-1,8-naphthyridine-3-carboxylic acid ethyl ester.

This ester 400 mg (1.06 mmoles) was suspended in 1 mL water, 1,9 mL 1N aqueous sodium hydroxide was added. The suspension was refluxed 30 minutes. The solution was cooled and adjusted to pH 7.5 with 1N hydrochloric acid. The precipitate was filtered and washed with water. The crude product was recrystalized in water to give 248 mg of titled compound. MP>270° C.

The following compounds were also prepared by following substantially the above procedure.

EXAMPLE 21

7-(3-METHYL-1-PIPERAZINYL)-1-(1,1-DIMETHYLETHYL)-1,4-DIHYDRO-6-FLUORO-4-OXO-1,8-NAPHTHYRIDINE-3-CARBOXYLIC ACID

EXAMPLE 22

7-(1S,4S-2,5-DIAZABICYCLO[2.2.1]HEPTAN-2-YL)-1-(1,1-DIMETHYLETHYL)-1,4-DIHYDRO-6-FLUORO-4-OXO-1,8-NAPHTHYRIDINE-3-CARBOXYLIC ACID. MP 250° C., [α]$^D$= −196° (c=0.25, 0.1N HCl)

EXAMPLE 23

7-(1S,4S-2,5-DIAZABICYCLO[2.2.2]OCTAN-2-YL)-1-(1,1-DIMETHYLETHYL)-1,4-DIHYDRO-6-FLUORO-4-OXO-1,8-NAPHTHYRIDINE-3-CARBOXYLIC ACID. MP 268° C.

EXAMPLE 24

7-(4-(CYCLOPENTEN-3-YL)-1-PIPERAZINYL)-1-(1,1-DIMETHYLETHYL)-1,4-DIHYDRO-6-FLUORO-4-OXO-1,8-NAPHTHYRIDINE-3-CARBOXYLIC ACID. MP 222° C.

EXAMPLE 25

7-(3-(AMINOMETHYL)-1-PYRROLIDINYL)-1-(1,1-DIMETHYLETHYL)-1,4-DIHYDRO-6-FLUORO-4-OXO-1,8-NAPHTHYRIDINE-3-CARBOXYLIC ACID. MP 254° C.

EXAMPLE 26

7-(3-((ETHYLAMINO)METHYL)-1-PYRROLIDINYL)-1-(1,1-DIMETHYLETHYL)-1,4-

DIHYDRO-6-FLUORO-4-OXO-1,8-NAPHTHYRIDINE-3-CARBOXYLIC ACID. MP 254° C.

EXAMPLE 27

7-(3-METHYL-1-PIPERAZINYL)-1-(1,1-DIMETHYLETHYL)-1,4-DIHYDRO-6-FLUORO-4-OXO-1,8-NAPHTHYRIDINE-3-CARBOXYLIC ACID. MP 205° C.

EXAMPLE 28

7-(3,4-DIMETHYL-1-PIPERAZINYL)-1-(1,1-DIMETHYLETHYL)-1,4-DIHYDRO-6-FLUORO-4-OXO-1,8-NAPHTHYRIDINE-3-CARBOXYLIC ACID. MP 204° C.

EXAMPLE 29

7-(3-PHENYL-1-PIPERAZINYL)-(1,1-DIMETHYLETHYL)-1,4-DIMETHYLETHYL)-1,4-DIHYDRO-6-FLUORO-4-OXO-1,8-NAPHTHYRIDINE-3-CARBOXYLIC ACID, METHANESULFONATE.

EXAMPLE 30

7-(1R,4R-2,5-DIAZABICYCLO[2.2.1]HEPTAN-2-yl)-1-(1,1-DIMETHYLETHYL)-1,4-DIHYDRO-6-FLUORO-4-OXO-1,8-NAPHTHYRIDINE-3-CARBOXYLIC ACID.

To a suspension of 440 mg (1.69 mmoles) 1R,4R-2,5-diazabicyclo[2.2.1]heptane, dihydrobromide and 418 mg (1.28 mmoles) 1-(1,1 dimethylethyl)-1,4-dihydro-6-fluoro-7-chloro-4-oxo-1,8-naphthyridine-3-carboxylic acid ethyl ester in 8 mL pyridine was added 0.67 g (4.4 mmoles) 1,8-diazabicyclo[5.4.0]undec-7-ene. The solution was refluxed 4 hours, evaporated to dryness under reduced pressure. The residue was taken in cold water. The precipitate was filtered to give 193 mg of 7-(1R,4R-2,5-diazabicyclo[2.2.1]heptan-2-yl)-1-(1,1-dimethylethyl)-1,4-dihydro-6-fluoro-4-oxo-1,8-naphthyridine-3-carboxylic acid ethyl ester.

This ester 193 mg (without further purification) was suspended in 1,96 mL 1N aqueous sodium hydroxide and refluxed 30 minutes. The solution was cooled and brought to pH 7.5 with 6N hydrochloric acid. The precipitate was filtered and washed three times with water and two times with ether to give 170 mg of titled compound. MP 250° C. $[\alpha]^D = +173°$ (c=0.25, 0.1N HCl) Methanesulfonate salt, MP 304° C., $[\alpha]^D = +158.6°$ (c=0.25, 0.1N HCL).

EXAMPLE 31

The following compound was prepared by following substantially the procedure of Example 30:
7-(1R,4R-5-METHYL-2,5-DIAZABICYCLO[2.2.1]HEPTAN-2-YL)-1-(1,1-DIMETHYLETHYL)-1,4-DIHYDRO-6-FLUORO-4-OXO-1,8-NAPHTHYRIDINE-3-CARBOXYLIC ACID The following compound was also prepared by the above procedure of Example 30 except that the condensation step lasted 24 hours:

EXAMPLE 32

7-(8-METHYL-3,8-DIAZABICYCLO[3.2.1]OCTAN-3-YL)-1-(1,1-DIMETHYLETHYL)-1,4-DIHYDRO-6-FLUORO-4-OXO-1,8-NAPHTHYRIDINE-3-CARBOXYLIC ACID, METHANESULFONATE SALT.

EXAMPLE 33

7-(3,8-DIAZABICYCLO[3.2.1]OCTAN-3-YL)-1-(1,1-DIMETHYLETHYL)-1,4-DIHYDRO-6-FLUORO-4-OXO-1,8-NAPHTHYRIDINE-3-CARBOXYLIC ACID, METHANESULFONATE

A mixture of 653 mg (2 mmoles) 1-(1,1-dimethylethyl)-1,4-dihydro-6-fluoro-7-chloro-4-oxo-1,8-naphthyridine-3-carboxylic acid ethyl ester and 732 mg (3 mmoles) 8-trifluoroacetyl-3,8-diazabicyclo[3.2.1]octan,-hydrochloride and 985 mg (6.48 mmoles) 1,8-diazabicyclo[5.4.0] undec-7-ene in 30 mL acetonitrile was heated at 60° C. for 72 hours. The solution was cooled and evaporated to dryness. The residue was worked up with dichloromethane and water. The organic layer was dried over magnesium sulfate and evaporated to give an oil. Purification was achieved by silicagel column chromatography to obtain 220 mg of 7-(8-trifluoroacetyl-3,8-diazabicyclo[3.2.1]octan-3-yl)-1-(1,1-dimethylethyl)-1,4-dihydro-6-fluoro-4-oxo-1,8-naphthyridine-3-carboxylic acid ethyl ester. MP 205° C.

The above ester (200 mg) was suspended in 1.64 mL 1N aqueous sodium hydroxyde for three hours. The solution was cooled and the pH adjusted to 7.4 with 2N hydrochloric acid. The precipitate was filtered, dissolved in 25 mL methanol, 27 μL methanesulfonic acid was added, the suspension was heated to reflux, filtered while hot, cooled. The precipite was filtered to give 100 mg of titled compound. MP 300° C.

EXAMPLE 34

The following compound was also prepared by the above procedure except that after alkaline hydrolysis and the pH adjusted to 7.4, the solution, after filtration, was evaporated to dryness. The residue was recrystallized in a mixture of isopropanol-ethanol 60/40:
7-(2-AMINOMETHYL-MORPHOLIN-4-YL)-1-(1,1-DIMETHYLETHYL)-1,4-DIHYDRO-6-FLUORO-4-OXO-1,8-NAPHTHYRIDINE-3-CARBOXYLIC ACID.

EXAMPLE 35

The following compound was prepared by following substantially the procedure of Example 33:
7-(3-AMINO-3-METHYL-PYROLIDIN-1-YL)-1-(1,1-DIMETHYLETHYL)-6-FLUORO-1,4-DIHYDRO-4-OXO-1,8-NAPHTHYRIDINE-3-CARBOXYCLIC ACID. MP>260° C.

EXAMPLE 36

7-(3-AMINO-1-PYRROLIDINYL)-1-(1,1-DIMETHYLETHYL)-1,4-DIHYDRO-6-FLUORO-4-OXO-1,8-NAPHTHYRIDINE-3-CARBOXYLIC ACID

To a suspension of 327 mg (1 mmole) 1-(1,1-dimethylethyl)-1,4-dihydro-6-fluoro-7-chloro-4-oxo-1,8-naphthyridine-3-carboxylic acid ethyl ester in 33 mL acetonitrile was added successively 615 mg (3 mmoles) of 3-trifluoroacetylaminopyrrolidine, hydrochloride and 415 mg (3 mmoles) anhydrous potassium carbonate. The suspension was stirred overnight and evaporated to dryness. The residue was taken up in 7 mL water, filtered and washed three times with 5 mL water recrystallized in ethanol to give 400 mg of 7-(3-trifluoroacetylamino-1-(1-pyrrolidinyl))-1-(1,1-dimethylethyl)-1,4-dihydro-6-fluoro-4-oxo-1,8-naphthyridine-3-carboxylic acid ethyl ester. MP 240° C.

This ester (370 mg-0.78 mmole) was suspended in 3.1 mL 1N aqueous sodium hydroxide and refluxed one hour. The solution was cooled and adjusted to pH 7.8 with 1N HCl. The precipitate was filtered and washed with water to give 250 mg of titled compound. MP 260° C. dec.

EXAMPLE 37

7-(3-FLUOROMETHYL-PIPERAZIN-4-YL)-1-(1,1-DIMETHYLETHYL)-1,4-DIHYDRO-6-FLUORO-4-OXO-1,8-NAPHTHYRIDINE-3-CARBOXYLIC ACID

This compound was prepared by following substantially the procedure of example 33 except the reaction lasted one hour.

EXAMPLE 38

7-(3-AMINOMETHYL-PIPERAZIN-4-YL)-1-(1,1-DIMETHYLETHYL)-1,4-DIHYDRO-6-FLUORO-4-OXO-1,8-NAPHTHYRIDINE-3-CARBOXYLIC ACID

This compound was prepared by following substantially the procedure of example 32.

EXAMPLE 39

7-(3-FLUOROMETHYL-PIPERAZIN-4-YL)-1-(1,1-DIMETHYLETHYL)-1,4-DIHYDRO-6-FLUORO-4-OXO-3-QUINOLINE-CARBOXYLIC ACID

This compound was prepared according to example 19.

EXAMPLE 40

7-(1,4-DIAZABICYCLO[3.2.1]OCT-4-YL)-1-(1,1-DIMETHYLETHYL)-1,4-DIHYDRO-6-FLUORO-4-OXO-1,8-NAPHTHYRIDINE-3-CARBOXYLIC ACID

This compound was prepared according to example 36. (The condensed amine was prepared by following the procedure described by P. A. STURM, M. CORY, D. W. HENRY, J. W. McCALL and J. B. ZIEGLER in J. Med. Chem. 1977, 20, 1333).

EXAMPLE 41

7-(3,8-DIAZABICYCLO [3.2.1] OCT-8-YL)-1-(1,1-DIMETHYLETHYL)-1,4-DIHYDRO-6-FLUORO-4-OXO-1,8-NAPHTHYRIDINE-3-CARBOXYLIC ACID (a) 7-(3,-benzyl-3,8-diazabicyclo [3.2.1] oct-8-yl)-1-(1,1-dimethylethyl)-1,4-dihydro-6-fluoro-4-oxo-1,8-naphthyridine-3-carboxylic acid ethyl ester was mainly obtained according to procedure described in example 33 by condensing 3-benzyl-3,8-diazabicyclo [3.2.1] octane, dihydrochloride with the corresponding 1-(1,1-dimethylethyl) naphthyridine in presence of 1,8-diazabicyclo [5.4.0] undec-7-ene in acetonitrile.

(b) This benzyl product was hydrogenized in methanol in presence of 10% palladium on carbon to give 7-(3,8-diazabicyclo [3.2.1] oct-8-yl)-1-(1,1-dimethylethyl)-1,4-dihydro-6-fluoro-4-oxo-1,8-naphthyridine-3-carbocylic acid ethyl ester which was hydrolyzed according to the procedure described in example 33 to give the title compound.

EXAMPLE 42

7-(3-AMINO-4-METHYL-1-PYRROLIDINYL)-1-(1,1-DIMETHYLETHYL)-1,4-DIHYDRO-6-FLUORO-4-OXO-1,8-NAPHTHYRIDINE-3-CARBOXYLIC ACID (CIS and TRANS MIXTURE)

This compound was obtained as described in example 36. M.P. 270° C.

EXAMPLE 43

7-(4-AMINOMETHYL-3-HYDROXY-1-PYRROLIDINYL)-1-(1,1-DIMETHYLETHYL)1,4-DIHYDRO-6-FLUORO-4-OXO-1,8-NAPHTHYRIDINE-3-CARBOXYLIC ACIDHYDROCHLORIDE

This compound was obtained according to the procedure described in example 33.

EXAMPLE 44

7-(4-AMINOMETHYL-3-HYDROXY-1-PYRROLIDINYL)-1-(1,1-DIMETHYLETHYL)-1,4-DIHYDRO-6-FLUORO-4-OXO-QUINOLINE-3-CARBOXYLIC ACID

This compound was obtained as described in example 19.

PREPARATION OF NEW AMINES

EXAMPLE A 1-(4-TOLUENESULFONYL)-4-HYDROXY-D-PROLINE ETHYL ESTER

To a cold solution of 10 g (50 mmoles) of 4-hydroxy-D-proline ethyl ester, hydrochloride (prepared according to G. L. BAKER; S. J. FRITSCHEL; J. R. STILLE and J. K. STILLE; J. Org. Chem. 1981, 46,2954) in 100 mL dry pyridine at +5° C. was added portionwise 10.66 g (56 mmoles) of 4-toluenesulfonyl chloride.

The resulting dark solution was stirred 24 h at +5° C. and evaporated to dryness. The residue was taken up in 2000 mL dichloromethane and was washed with 2N hydrochloric acid then with water. The organic layer was dried over MgSO$_4$, filtered and evaporated to dryness. The oily residue was crystallized in diisopropyl ether to yield 13.70 g of titled compound. MP 78° C. $[\alpha]^{20} = +79.39°$ (c=1.8, ethanol)

1-(4-TOLUENESULFONYL)-4-(4-TOLUENESULFONYLOXY)-D-PROLINE ETHYL ESTER

To a cold solution of 11.85 g (38 mmoles) 1-(4-toluenesulfonyl)-4-hydroxy-D-proline ethyl ester in 37 mL pyridine at 0° C. was added 8.0 g (41 mmoles) of 4-toluenesulfonyl chloride portionwise in 15 minutes. The cold solution was stirred one hour at 0° C. and then 48 h at room temperature. Water (100 mL) was added dropwise in the solution cooled at 0° C. which was stirred 30 minutes at 0° C. The precipitate was filtered and washed with cold water and ether to give 15.55 g of titled compound. MP 122° C. $[\alpha]^{20} = +26.36°$ (c=2, chloroform)

1-(4-TOLUENESULFONYL)-4-(4-TOLUENESULFONYLOXY-2-HYDROXYMETHYLPYRROLIDINE

To a stirred solution of 4.67 g (10 mmoles) 1-(4-toluenesulfonyl)-4-(4-toluenesulfonyloxy)-D-proline ethyl ester in 45 mL tetrahydrofuran at 0° C. was added 0.77 g (35 mmoles) of lithium borohydride. The suspension was stirred one hour at 0° C. and then one hour at room temperature. More lithium borohydride 0.15 g (6.9 mmoles) was added and the suspension was stirred overnight at room temperature.

The suspension was cooled at 0° C. and 5N hydrochloric acid was added dropwise until no gas released.

The suspension was evaporated to dryness under reduced pressure. The residue was taken up in water and ethylacetate. The organic layer was washed with little water and brine, dried over MgSO4 and evaporated to dryness under reduced pressure to afford 4.16 g of titled compound. MP 93° C.; $[\alpha]^D = +14°$ (c=2, ethanol).

1-(4-TOLUENESULFONYL)-2-(4-TOLUENESULFONYLOXYMETHYL)-4-(4-TOLUENESULFONYLOXY)-PYRROLIDINE

To a cooled solution of 1.83 g (9.6 mmoles) 4-toluenesulfonyl chloride in 10 mL pyridine at +10° C. was added 3.40 g (8 mmoles) of 1-(4-toluenesulfonyl)-2-hydroxymethyl-4-(4-toluenesulfonyloxy)-pyrrolidine and the mixture was stirred 18 hours. The solution obtained was then poured into 50 mL ice-cooled 2N hydrochloric acid. The precipitate was filtered, washed with water and ether. The crystalline product was purified in boiling water and ether. The crystalline product was purified in boiling ethanol to give 3.94 g of titled compound. MP 153° C. $[\alpha]^D = +46.7°$ (c=1.9, acetone).

1R,4R-2-(4-TOLUENESULFONYL)-5-PHENYLMETHYL-2,5-DIAZABICYCLO-(2.2.1)HEPTANE

A mixture of 3.6 g (6.2 mmoles) 1-(4-toluenesulfonyl)-2-(4-toluenesulfonyloxymethyl)-4-(4-toluenesulfonyloxy)-pyrrolidine and 1.99 g (18 mmoles) of benzylamine in 12 mL toluene was heated under reflux for 72 hours. The mixture was cooled, the benzylamine toluenesulfonate was filtered off. The filtrate was evaporated to dryness and flash chromatographied with dichloromethane-ethyl acetate 70:30 to yield 0.74 g titled compound. mp 118° C.; $[\alpha]^D = +13.9°$ (c=0.4, chloroform).

1R,4R-5-PHENYLMETHYL-2,5-DIAZABICYCLO-(2.2.1)HEPTANE, DIHYDROBROMIDE

To a hot solution of 17 mL hydrobromic acid 33% in acetic acid at 70° C. was added 1 g (2.9 mmoles) of 1R,4R-2-(4-toluenesulfonyl)-5-phenylmethyl-2,5-diazabicyclo (2.2.1) heptane. The solution was stirred for 12 hours at 70° C. The suspension was cooled and concentrated to one third, cooled to 10° C. The precipitate was filtered, washed with acetic acid and acetone to afford 0.9 g of titled compound. MP 275° C.; $[\alpha]^D = -0.38°$ (C=1, H2O)

1R,4R-2,5-DIAZABICYCLO-(2.2.1)HEPTANE, DIHYDROBROMIDE

A suspension of 6.6 g (18.8 mmoles) 1R,4R-5-phenylmethyl-2,5-diazabicyclo(2.2.1)heptane dihydrobromide and 3.0 g 10% Pd on C was hydrogenated at atmospheric pressure. The reaction was complete in about 4 hours. The catalyst was filtered off and the filtrate was evaporated. The residue was slurried in ethanol, filtered to give 4.34 g of titled compound. $[\alpha]^D = -20.4°$ (c=1.2, 0.1N HCl)

EXAMPLE B

2-(N-PHTHALIMIDE)METHYL-4-PHENYLMETHYLMORPHOLINE

A suspension of 6.42 g (28.4 mmoles) 2-chloromethyl-4-phenylmethyl morpholine (prepared according to F. LOFTUS, Synth. Communications, 10 (1), 59 (1980)) and 5.18 g (28.0 mmoles) of potassium phthalimide in 15 mL dry dimethylformamide were stirred 48 hours at 120°-130° C. The suspension was cooled and poured into ice-water, extracted twice with ethyl acetate, washed with brine, dried over MgSO4. The residue was recrystallized from isopropanol to yield 6.54 g of titled compound. MP 133° C.

2-AMINOMETHYL-4-PHENYLMETHYLMORPHOLINE

A suspension of 3.36 g (10 mmoles) 2-(N-phthalimido)methyl-4-phenyl methylmorpholine was refluxed with 1.25 g (25 mmoles) of hydrazine hydrate 85% in 50 mL ethanol for two hours. The suspension was cooled and then filtered off. The filtrate was evaporated to dryness, taken up with ether, filtered again and the filtrate concentrated under vacuum to give 2.05 g of titled compound as an yellow oil.

2-(N-TRIFLUOROACETHYL)AMINOMETHYL-4-PHENYLMETHYLMORPHOLINE

A mixture of 6.18 g (30 mmoles) 2-aminomethyl-4-phenylmethylmorpholine and 20 mL trifluoroacetic anhydride was refluxed 15 minutes. The mixture was cooled, and evaporated to dryness. The residue was taken up in ethyl acetate, washed with ice cooled 1N aqueous sodium hydroxyde, water and brine, dried over MgSO4 and evaporated to dryness. The residue was crystallized in ether to afford 7.84 g of titled compound. MP 118° C.

2-(N-TRIFLUOROACETYL)AMINOMETHYL-MORPHOLINE,HYDROCHLORIDE

A suspension of 7.92 g (26.2 mmoles) 2-(trifluoroacetyl)aminomethyl-4-phenylmethyl morpholine and 1.7 g 10% Pd on C was hydrogenated at atmospheric pressure. The reaction was complete in about 3 hours. The catalyst was filtered off and the filtrate was evaporated to dryness and 4.92 mL ethanolic 5N hydrochloric acid was added to the oily product in 50 mL ethanol. The solution was evaporated to dryness and crystallized by scratching in ether to yield 4.19 g of crude product which was recrystallized in isopropanol to give 2.82 g of titled compound. MP 186° C.

EXAMPLE C

3-BENZYL-2,4-DIOXO-3,8-DIAZABICYCLO(3.2.1)OCTANE

A mixture of 3-benzyl-2,4-dioxo-8-methyl-3,8-diazabicyclo-(3.2.1)octane (U.S. Pat. No. 3,328,396) (1.05 g) and pyridinium hydrochloride (5 g) was heated in an oil-bath at 220° C. for 25 minutes. After cooling, the mixture was taken up with water (30 mL) and extracted with ether. The organic layer was dried over magnesium sulfate, evaporated to give 0.45 g of crude product which was chromatographed over silica gel using dichloromethane-ethyl acetate 80:20 as eluent to give 0.3 g of crystallized titled product. MP 72° C.

3-BENZYL-3,8-DIAZABICYCLO(3.2.1)OCTANE

A solution of 3-benzyl-2,4-dioxo-8-methyl-3,8-diazabicyclo (3.2.1)octane (2.05 g, 8.91 mmoles) in dry ether (100 mL) was treated gradually with lithium aluminum hydride (1.52 g, 4 mmoles), heated under reflux for one hour, and hydrolyzed successively with 50 mL of water-saturated ether and then 10 mL of water. This mixture was filtered on a celite pad. The filtrate was dried over magnesium sulfate and then evaporated to give the crude titled product which was used without any purification for further uses.

3-BENZYL-8-TRIFLUOROACETYL-3,8-DIAZABICYCLO(3.2.1)OCTANE, HYDROCHLORIDE

Trifluoroacetatic acid anhydride (4.6 mL) was added to ice-cooled 3-benzyl-3,8-diazabicyclo(3.2.1)octane (1.4 g, 6.9 mmoles). The resulting mixture was heated under reflux for 15 minutes, cooled, diluted with ethanol (20 mL) and treated with 2 mL of 5N hydrochloric acid in ethanol, evaporated to dryness. The so-obtained solid was taken-up with ether, collected by filtration, and dried in vacuo to afford 1.6 g of titled compound. MP 176° C.

8-TRIFLUOROACETYL-3,8-DIAZABICYCLO(3.2.1)OCTANE

A solution of the 3-benzyl-8-trifluoroacetyl-3,8-diazabicyclo-(3.2.1)octane hydrochloride in 50 mL of methanol was hydrogenated at atmospheric pressure in the presence of 10% Pd/C (0.5 g) until the theoretical quantity of hydrogen was absorbed. The mixture was filtered and the filtrate was evaporated to dryness to yield 1.08 g of titled compound as a white solid. MP 224° C. (dec).

EXAMPLE D

1-(CYCLOPENTEN-3-YL)PIPERAZINE 3-chlorocyclopentene (306 mmoles, 36.9 g) was added dropwise to a solution of anhydrous piperazine (496 mmoles, 36.9 g) in dry methanol (350 mL) at −13° C. The final solution was stirred at −13° C. for 15 minutes and at room temperature for one hour. The solvent was evaporated to dryness, and the residue was first taken up with chloroform and then filtered to eliminate the precipitate. After elimination of chloroform by evaporation the filtrate give 10 g of 1-(cyclopenten-3-yl) piperazine (yellow oil).

EXAMPLE E

2-CARBOXYETHYL-1,4-DI-PHENYLMETHYL PIPERAZINE

To a solution of 43.29 g (166.0 mmol) of ethyl 2,3-dibromopropionate in 145 ml of benzene warmed at 40° C. was added dropwise a solution of 40 g (166.0 mmol) of N,N'-dibenzylethylenediamine and 46.2 ml (166.0 mmol) of triethylamine in 40 ml of benzene. The vigourous stirred suspension was heated under reflux overnight, cooled and filtered. The benzene layer was washed three times with 50 ml of water. The organic layer was dried over magnesium sulfate. After evaporation 58.95 g of a thick oil was obtained which was purified by chromatography using dichloromethane/ethyl acetate (90:10) to yield 50.4 g (89.7%) of title compound.

2-HYDROXYMETHYL-1,4-DI-PHENYLMETHYL PIPERAZINE

In a dry flask were carefully placed 5.67 g (150 mmol) of lithium aluminum hydride to which were added 110 ml of absolute ether. The suspension was flushed with nitrogen and cooled to −5° C. Then a solution of 25 g (73.0 mmol) of 2-carboxyethyl-1,4-di-phenylmethyl pi-piperazine in 110 ml of absolute ether was added dropwise. After complete addition the suspension was heated under reflux for three hours, cooled in an ice-bath. Excess of hydride was carefully destroyed with 6.3 ml of water. Insoluble material was filtered off and the ether layer was washed with water and dried over magnesium sulfate. After removing of the solvent it was obtained 18.85 g. (86%) of title compound. MP 77° C.

2-FLUOROMETHYL-1,4-DI-PHENYLMETHYL PIPERAZINE

To a solution of 0.6 g (3.7 mmol) of diethylamino-sulfur trifluoride in 5 ml dichloromethane cooled at −78° C. under nitrogen was added dropwise a solution of 1 g (3.4 mmol) of 2-hydroxymethyl-1,4-diphenylmethyl piperazine in 5 ml dichloromethane. The temperature of the solution was allowed to warm to −50° C. in 30 mn then to C. in 1 hr 30 min. The solution was stirred two more hours at room temperature and cooled back to +5° C. A few drops of aqueous saturated solution of sodium bicarbonate were added until basic pH. The organic layer was washed twice with water, dried over magnesium sulfate, the solvent removed to give 1.10 g of an oil which was purified by chromatography using dichloromethane/ethyl acetate (95:5) to afford 0.46 g (42%) of title compound.

2-FLUOROMETHYL-PIPERAZINE, DIHYDROCHLORIDE

A solution of 0.44 g (1.47 mmol) of 2-fluoromethyl-1,4-di-phenylmethyl piperazine in 20 ml ethanol was hydrogenized over 0.2 g of 10% palladium on carbon for 4 hours. The catalyst was filtered over a celite pad, washed with water. To the filtrat was added 3.2 ml of 1N aqueous hydrochloric acid. The solution was evaporated to dryness, taken up twice with absolute ethanol. The residue was crystallized in the minimum amount of absolute ethanol to give 0.22 g of white crystals of title compound (69%). M.P. 232° C.

EXAMPLE F

2-CHLOROMETHYL-1,4-DI-PHENYLMETHYL PIPERAZINE

A suspension of 23 g (62.3 mmol) of 2-hydroxymethyl-1,4-di-phenylmethyl piperazine, dihydrochloride in 79 ml thionyl chloride was heated 4 hours under reflux. The solution was cooled and excess thionyl chloride was evaporated under reduced pressure. The residue was crystallized in ethanol, dried with acetone to yield 19.5 g of title compound dihydrochloride M.P. 234° C. dec. A suspension of this dihydrochloride in 130 ml 1N aqueous sodium hydroxyde was stirred with 75 ml dichloromethane, the aqueous layer back washed three times with 75 ml dichloromethane. The organic layers were collected and dried over magnesium sulfate to give after evaporation 15.44 g (78%) of title compound.

2-PHTALIMIDOMETHYL-1,4-DI-PHENYLMETHYL PIPERAZINE

A suspension of 15 g (47.6 mmol) of 2-chloromethyl-1,4-diphenylmethyl piperazine and 8.81 g (47.6 mmol) of potassium phtalimide in 7 ml anhydrous dimethyl formamide was stirred 2 hours at 110° C. After cooling the reaction mixture was taken up with 100 ml ethyl acetate. The mineral salts were filtered off. The solvent was removed, the residue was dissolved in 150 ml ethyl acetate, washed three times with water, dried over magnesium sulfate to give a srystalline product which was resrystallized in isopropyl ether to yield 6.67 g (33%) of title compound. M.P. 124° C.

2-AMINOMETHYL-1,4-DI-PHENYLMETHYL PIPERAZINE

The solution of 4.25 g (10 mmol) of 2-phtalimidomethyl-1,4-di-phenylmethyl piperazine and 1.25 g (25 mmol) of hydrazine monohydrate in 50 ml ethanol was stirred 2 hours under reflux. Insoluble material was filtered off. The ethanol layer was evaporated to dryness to afford a residue taken up in 20 ml ethyl ether, filtered again and evaporated to give 3.0 g of the title compound as an oil.

2-TRIFLUOROACETYLAMINOMETHYL-1,4-DI-PHENYLMETHYL PIPERAZINE, DIHYDROCHLORIDE

A suspension of 2.9 g (10 mmol) of 2-aminomethyl-1,4-di-phenylmethyl piperazine in 10 ml of trifluoroacetic anhydride was heated to reflux for 15 mn, cooled and evaporated to dryness. The residue was taken up in 40 ml ethanol and 5 ml 5N hydrochloric acid in ethanol. The solution was evaporated to dryness. The residue was triturated in 30 ml ethyl ether, the crystals were filtered and dried to give 3.98 g raw material, which was purified by dissolving impurities in hot acetone to yield 3.11 g of the title compound.

2-TRIFLUOROACETYLAMINOMETHYL PIPERAZINE

To a solution of 3.1 g (6.7 mmol) of 2-trifluoroacetylaminomethyl-1,4-diphenylmethyl piperazine dihydrochloride in 100 ml methanol was added a suspension of 0.5 g palladium on carbon in 2 ml water. The mixture was hydrogenized for 30 mn, the catalyst was filtered off and the solvent was removed, taken up in 10 ml absolute ethanol, evaporated again and crystallized in ether to yield 1.37 g of a white powder (72%) as title compound.

EXAMPLE G

3-BENZYL-2,4-DIOXO-3,8-DIAZABICYCLO [3.2.1] OCTANE

In a dry flask were mixed 15 g of dry pyridine hydrochloride and 3.15 g (130 mmol) of 3-benzyl-2,4-dioxo-8-methyl-3,8-diazabicyclo [3.2.1] octane prepared according to U.S. Pat. No. 3,328,398 in 1967, Jun. 27. The mixture was heated in an oil bath preheated at 220° C. for 20 mn, cooled in an ice-bath, dissolved in 90 ml water, extracted four times with 100 ml ethyl ether. The organic layers were collected and dried over magnesium sulfate. After removing the solvent, the residue was chromatographied over silica-gel using dichloromethane/ethylacetate (80:20) to afford 1.5 g of the title compound (50%). M.P. 72° C.

3-BENZYL-3,8-DIAZABICYCLO [3.2.1] OCTANE, DIHYDROCHLORIDE

In a dry flask were carefully placed 1.5 g (39.5 mmol) of lithium aluminum hydride to which were added 100 ml absolute ethyl ether. The suspension was flushed with nitrogen and cooled to 0° C. Then 1.7 g (7.4 mmol) of 3-benzyl-2,4-dioxo-3,8-diazabicyclo [3.2.1] octane was added portions wise for 15 mn. The mixture was heated under reflux for 3 hours, cooled, and washed up with water. The reaction mixture was filtered over a celite pad. The solvant was removed and the oily product was transformed as its dihydrochloride to yield 1.54 g (59%) of title compound. M.P. 158° C.

EXAMPLE H

3-HYDROXY-4-AMINOCARBONYL-1-PHENYLMETHYL PYRROLIDINE

A solution of 11.0 g (44.0 mmol) of 3-hydroxy-4-ethyloxycarbonyl-1-phenylmethyl pyrrolidine (prepared according to E. JAEGER and J. H. BIEL in J. Org. Chem. 1965, 30, (740) in 40 g of 25% ammonia in methanol was heated at 100° C. under pressure overnight. The solution was cooled and evaporated to dryness. The oily residue was purified by chromatography using dichloromethane-methanol (85:15) to yield 2.14 g (22%) of the title compound. M.P. 128° C.

3-HYDROXY-4-AMINOMETHYL-1-PHENYLMETHYL PYRROLIDINE

In a dry flask was place 1.34 g (35.0 mmol) of lithium aluminum hydride in 20 ml dry tetrahydrofuran cooled to −5° C. To this suspension was added dropwise 2.58 g (11.7 mmol) of 3-hydroxy-4-aminocarbonyl-1-phenylmethyl pyrrolidine. After completion of addition the suspension was warmed 2 hours under reflux, cooled. It was successively added 35 ml dichloromethane, 50 ml tetrahydrofuran and 2.3 ml water. The suspension was passed through a celite pad. The solvent removed to give 2.19 g (90.8%) of title compound as an oil.

3-HYDROXY-4-AMINOMETHYL-PYRROLIDINE, DIHYDROCHLORIDE

A solution of 2.19 g (10.6 mmol) of 3-hydroxy-4-aminomethyl-1-phenylmethyl pyrrolidine in 60 ml anhydrous methanol and 5.3 ml 5N hydrochloric acid in ethanol was hydrogenized over 1.83 g palladium on carbon for 17 hours. The catalyst was filtered off, the solvent removed to afford 1.39 g (70%) of title compound.

PREPARATION OF QUINOLONE AND NAPHTHYRIDONE INTERMEDIATES

EXAMPLE I 3-(2,4-DICHLORO-5-FLUOROPHENYL)-3-OXO-2-(((1,1-DIMETHYLETHYL)AMINO)METHYLENE)-PROPANOIC ACID ETHYL ESTER

A solution of 0.95 mL of tert-butylamine (9 mmoles) in 2 mL of dry ethanol was added to 3.02 g (9 mmoles) of 3-(2,4-dichloro-5-fluorophenyl)-3-oxo-2-ethoxymethylenepropanoic acid ethyl ester in 10 mL of dry ethanol at −5° C.

The resulting mixture was stirred at room temperature for one hour. The resulting precipitate was collected by filtration and washed with 3 mL of ethanol and 5 mL of petroleum ether to afford 1.35 g of 3-(2,4-dichloro-5-fluorophenyl)-3-oxo-2-(((1,1-dimethylethyl)amino)methylene)-propanoic acid ethyl ester. MP 87° C.

The residual filtrate was evaporated to dryness. The resulting mixture (oil+solid) was crystallized in 3 mL of isopropanol to give 1.06 g more product. MP 88°–89° C.

EXAMPLE II 3-(2,3,4,5-TETRAFLUOROPHENYL)-3-OXO-2-(((1,1-DIMETHYLETHYL)AMINO)METHYLENE)-PROPANOIC ACID ETHYL ESTER

A solution of 1.77 g (24.2 mmoles) tert-butylamine in 2 mL ethanol was added to a mixture of 7.05 g (22 mmoles) of 3-(2,3,4,5-tetrafluorophenyl)-3-oxo-2-(ethoxymethylene)-propanoic acid ethyl ester and 9 mL ethanol cooled in a bath containing ice and salt. More ethanol (2.3 mL) was added and the mixture was stirred at room temperature for 2 hours. After cooling at 0° C., the resulting precipitate was filtered and washed with ethanol to give 3.72 g of titled compound. MP 112° C.

EXAMPLE III 3-(2,4,5-TRIFLUOROPHENYL)-3-OXO-2-(((1,1-DIMETHYLETHYL)AMINO)METHYLENE)-PROPANOIC ACID ETHYL ESTER

Tert-butylamine (6.2 mL, 84.7 mmoles) was added to a solution of 13.15 g (43.5 mmoles) of 3-(2,4,5-trifluorophenyl)-3-oxo-2-(ethoxymethylene)-propanoic acid ethyl ester in 19 mL of dry ethanol at −15° C. After 5 minutes, the mixture was stirred at room temperature for one hour, and then concentrated to dryness. The crude residue (10.87 g) was crystallized from 25 mL of hexane to afford 7.22 g of titled compound.

EXAMPLE IV

6,7,8-TRIFLUORO-1-(1,1-DIMETHYLETHYL)-1,4-DIHYDRO-4-OXO-3-QUINOLINE CARBOXYLIC ACID ETHYL ESTER

A mixture of 3.5 g (11 mmoles) of 3-(2,3,4,5-tetrafluorophenyl)-3-oxo-2-(((1,1-dimethylethyl)amino)methylene)-propanoic acid ethyl ester, 35 mL dioxane and 0.512 g (12.7 mmoles) of 60% sodium hydride was stirred at room temperature under nitrogen for 6 hours and then at 40°–50° C. for one hour.

The dioxane was eliminated. The residue was taken up with cold water, the resulting solid was filtered and dried to give a mixture which was chromatographed over 200 g of silicagel using toluene-ethylacetate 80:20 as eluent. There was collected 1.54 g of titled compound. MP 146° C.

EXAMPLE V

6,7-DIFLUORO-1,4-DIHYDRO-1-(1,1-DIMETHYLETHYL)-4-OXO-3-QUINOLINE CARBOXYLIC ACID ETHYL ESTER

There was added 1.1 g (27 mmoles) of 60% sodium hydride portionwise, at a temperature between 18° C. to 22° C., to a suspension of 7.22 g (21.9 mmoles) of 3-(2,4,5-trifluorophenyl)-3-oxo-2-(((1,1-dimethylethyl)amino)methylene)propanoic acid ethyl ester in 73 mL of anhydrous dioxane. An exothermic reaction occured. After stirring at room temperature during 1 hour, the resulting mixture was evaporated to dryness, and taken up with $CH_2Cl_2$ (150 mL) and $H_2O$ (200 mL). After decantation the organic layer was dried over $MgSO_4$. Evaporation of dichloromethane gave 6.41 g of an amorphous solid which was washed twice with water to yield 6.08 g of titled compound.

EXAMPLE VI

6-FLUORO-7-CHLORO-(1,1-DIMETHYLETHYL)-1,4-DIHYDRO-4-OXO-3-QUINOLINE CARBOXYLIC ACID

To a solution of 3-(2,4-dichloro-5-fluoro)-3-oxo-2-(((1,1-dimethyl ethyl)amino)methylene)propanoic acid ethyl ester in 10 mL dioxane at 7° C. under nitrogen was added portionwise 0.34 g (8.45 mmoles) of 60% sodium hydride. During the addition 9 mL more dioxane was added to help stirring. The final mixture was stirred for 30 minutes at room temperature and then heated under reflux for 2.25 hours. The solvent was evaporated in vacuo to give the crude ethyl ester of the titled compound. To this product was added 10 mL of water and 0.6 g of potassium hydroxide. This mixture was heated under reflux for 1.5 hours, cooled to room temperature, acidified to pH 1–2 with 6N hydrochloric acid. The resulting precipitate was collected by filtration, washed with water, and recrystallized from water (3 mL)+dioxane (60 mL) to give 0.8 g of 6-fluoro-7-chloro-(1,1-dimethylethyl)-1,4-dihydro-4-oxo-3-quinoline carboxylic acid. mp 274° C. (dec). Evaporation of the mother liquor gave a residue which was taken up with 15 mL boiling dioxane. After cooling and filtration 0.4 g more of titled carboxylic acid was obtained. MP 272°–273° C. (dec).

EXAMPLE VII

6,7-DIFLUORO-1-(1,1-DIMETHYLETHYL)-1,4-DIHYDRO-4-OXO-3-QUINOLINE CARBOXYLIC ACID

A mixture of 6.08 g (19.7 mmoles) of 6,7-difluoro-1-(1,1-dimethylethyl)-1,4-dihydro-4-oxo-3-quinolinecarboxylic acid ethyl ester and 19.7 mmoles of 2N aqueous sodium hydroxide in 80 mL of ethanol was stirred overnight. The resulting mixture was concentrated in vacuo, taken up with 200 mL of water and extracted with dichloromethane. About 8 mL of 2N HCl was added to the aqueous layer to adjust the pH to 3. The precipitate was collected by filtration, washed with $H_2O$ and dried to give 4.47 g, of titled compound. MP>260° C.

EXAMPLE VIII

3-(2,6-DICHLORO-3-FLUORO-5-PYRIDINYL)-3-OXO-2-(((1,1-DIMETHYLETHYL)AMINO)METHYLENE)-PROPANOIC ACID ETHYL ESTER

A solution of 10.8 g (148 mmoles) of tert-butylamine in 50 mL dry ethanol was added dropwise in about 30 minutes to a suspension of 50 g (148 mmoles) of 3-(2,6-dichloro-3-fluoro-5-pyridinyl)-3-oxo-2-(((1,1-dimethylethyl)amino)methylene)-propanoic acid ethyl ester in 125 mL dry ethanol at −5° C. under nitrogen. The mixture was stirred at room temperature for one hour. The solvent was evaporated. The resulting oil (54.3 g) was stirred in 100 mL of petroleum ether for 0.5 hour with cooling. The precipitated yellow solid was filtered, washed with petroleum ether, and dried in vacuo over phosphorous pentoxide to afford 47.7 g of titled compound. MP 78° C.

EXAMPLE IX

7-FLUORO-6-CHLORO-1,4-DIHYDRO-1(1,1-DIMETHYLETHYL)-4-OXO-1,8-NAPHTHYRIDINE-3-CARBOXYLIC ACID ETHYL ESTER

There was gradually added 1.3 g (32.4 mmoles) of 60% sodium hydride under nitrogen at room temperature to a solution of 10 g (27.5 mmoles) of 3-(2,6-dichloro-3-fluoro-5-pyridinyl)-3-oxo-2-(((1,1-dimethylethyl)amino)methylene)propanoic acid ethyl ester (10 g) in 34 mL dry dioxane 0.3 mL. The temperature raised spontaneously to +60° C. After stirring for 15 minutes, the solvent was eliminated in vacuo. The resulting solid was taken up with 100 mL dichloromethane and the mixture was chilled in an ice bath. After decantation, the organic layer was washed with cold water and dried over magnesium sulfate to afford 8.2 g of title compound. MP 155° C. (A sample washed with hexane melted at 158° C.).

EXAMPLE X

6-FLUORO-7-ETHYLTHIO-1,4-DIHYDRO-1-(1,1-DIMETHYLETHYL)-4-OXO-1,8-NAPHTHYRIDINE-3-CARBOXYLIC ACID ETHYL ESTER

Acetone (90 mL) was added to a mixture of 1.96 g (6 mmoles) of 6-fluoro-7-chloro-1-(1,1-dimethylethyl)-1,4-dihydro-4-oxo-1,8-naphthyridine-3-carboxylic acid ethyl ester and 2.5 g (18 mmoles) of anhydrous potassium carbonate. To this suspension was added 1.33 mL (18 mmoles) of ethanethiol. After heating to reflux for 2.5 hours, the solvent was eliminated in vacuo. The residue was taken up with ethylacetate and water. The organic layer was separated, washed with water and brine, and dried over magnesium sulfate. The resulting solid was treated with ether to give 1.67 g of titled compound. MP 159°–60° C.

EXAMPLE XI

6-FLUORO-7-ETHYLTHIO-1,4-DIHYDRO-1-(1,1-DIMETHYLETHYL)-4-OXO-1,8-NAPHTHYRIDINE-3-CARBOXYLIC ACID

A suspension of 0.23 g (0.65 mmoles) of 6-fluoro-7-ethylthio-(1,1-dimethylethyl)-1,4-dihydro-4-oxo-1,8-naphthyridine-3-carboxylic acid ethyl ester in 1 mL of water was treated with 1.3 mL of 1N aqueous sodium hydroxide and the mixture was heated under reflux for 45 minutes. The resulting precipitate was acidified with 1 mL of 2N hydrochloric acid, filtered, washed with water and dried in vacuo at 50° C. to give 0.196 g of titled compound. MP 215° C.

EXAMPLE XII

6-FLUORO-7-ETHYLSULFONYL-1-(1,1-DIMETHYLETHYL)-1,4-DIHYDRO-4-OXO-1,8-NAPHTHYRIDINE-3-CARBOXYLIC ACID

A suspension of 1.34 g (4.1 mmoles) of 7-ethylthio-6-fluoro-1-(1,1-dimethylethyl)-1,4-dihydro-4-oxo-1,8-naphthyridine-3-carboxylic acid in 20 mL acetic acid was cooled to +5° C. Then 2.5 mL 30% hydrogen peroxide was added dropwise. After the addition, the suspension was carefully warmed at 45° C. until a clear solution was obtained. The mixture was held at room temperature for 48 hours. The precipitate was filtered and washed with water and ether to give 0.90 g of titled compound. MP 207° C. (dec).

The following Table 1 illustrates the quinoline- and naphthyridine-carboxylic acid antibacterial compounds described above in Examples 1–44 which are represented by the structural formula at the top of the table.

The compounds of this invention display antibacterial activity when tested by the microtitration dilution method reported by Heifetz et al., Antimicr. Agents & Chemoth., 6. 124 (1974). Minimum inhibitory concentrations (MICs, in μg/ml) for but a few representative compounds according to this invention were determined by the above-mentioned method. The results are set forth in the following Table 2.

Quinoline analogs of Example 1 having 1,1-dimethylpropyl, 1-methylcyclopropyl, 1-methylcyclobutyl and isopropenyl substituents in the 1-position of the quinoline ring system were also prepared following substantially the procedures described herein. Representative quinolone compounds and naphthyridone compounds (generally as their methanesulfonate salts) were tested for in vitro biological activity, the results of which are described for Table 2. All of these compounds gave results indicating antibacterial activity somewhat less than that given by the compound of Example 1 but still a useful level of antibacterial activity. Naphthyridine analogs of Example 1 (corresponding to Example 20 having the substituents in the 1-position of the naphthyridine ring system described above with regard to the quinoline analogs) are also specifically contemplated and are expected to show improvement in antibacterial activity over their quinoline analogs comparable to the improvement illustrated by Example 20 relative to Example 1.

TABLE 1
LIST OF EXAMPLES

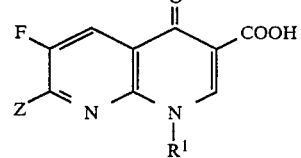

| Ex. | $R^1$ | Y | Z |
|---|---|---|---|
| 1 | $C(CH_3)_3$ | CH | 1-piperazinyl |
| 2 | " | " | 4-(cyclopenten-3-yl)-1-piperazinyl |
| 3 | " | " | 8-methyl-3,8-diazabicyclo[3.2.1]octan-3-yl |
| 4 | " | " | 3-phenyl-1-piperazinyl |
| 5 | " | " | 3-amino-3-methylpyrrolidin-1-yl |
| 6 | " | " | 4-methyl-1-piperazinyl |
| 7 | " | " | 2,5-diazabicyclo[2.2.2]octan-2-yl |
| 8 | " | " | 1S,4S-2,5-diazabicyclo[2.2.1]heptan-2-yl |
| 9 | " | " | 3-aminomethyl-1-pyrrolidinyl |
| 10 | " | " | 3-(ethylamino)methyl-1-pyrrolidinyl |
| 11 | " | " | 3-methyl-1-piperazinyl |
| 12 | " | " | 3,5-dimethyl-1-piperazinyl |
| 13 | " | " | 4-dimethylamino-1-piperazinyl |
| 14 | " | " | 1R,4R-2,5-diazabicyclo[2.2.1]heptan-2-yl |
| 15 | " | " | 4-(1,1-dimethylethyl)-1-piperazinyl |
| 16 | " | CF | 1-piperazinyl |
| 17 | " | CF | 3-(ethylamino)methyl-1-pyrrolidinyl |
| 18 | " | CF | 1R,4R-2,5-diazabicyclo[2.2.1]heptan-2-yl |
| 19 | " | CH | 3-amino-1-pyrrolidinyl |
| 20 | " | N | 1-piperazinyl |
| 21 | " | " | 3-methyl-1-piperazinyl |
| 22 | " | " | 1S,4S-2,5-diazabicyclo[2.2.1]heptan-2-yl |
| 23 | " | " | 2,5-diazabicyclo[2.2.2]octan-2-yl |
| 24 | " | " | 4-(cyclopenten-3-yl)-1-piperazinyl |
| 25 | " | " | 3-aminomethyl-1-pyrrolidinyl |
| 26 | " | " | 3-(ethylamino)methyl-1-pyrrolidinyl |
| 27 | " | " | 3-methyl-1-piperazinyl |
| 28 | " | " | 3,4-dimethyl-1-piperazinyl |
| 29 | " | " | 3-phenyl-1-piperazinyl |
| 30 | " | " | 1R,4R-2,5-diazabicyclo[2.2.1]heptan-2-yl |
| 31 | " | " | 1R,4R-5-methyl-2,5-diazabicyclo[2.2.1]-heptan-2-yl |
| 32 | " | " | 8-methyl-3,8-diazabicyclo[3.2.1]octan-3-yl |
| 33 | " | " | 3,8-diazabicyclo[3.2.1]octan-3-yl |
| 34 | " | " | 2-aminomethyl-morpholin-4-yl |
| 35 | " | " | 3-amino-3-methylpyrrolidin-1-yl |
| 36 | " | " | 3-amino-1-pyrrolidinyl |
| 37 | " | N | 3-fluoromethyl-piperazin-4-yl |
| 38 | " | N | 3-aminomethyl-piperazin-4-yl |
| 39 | " | CH | 3-fluoromethyl-piperazin-4-yl |
| 40 | " | N | 1,4-diazabicyclo[3.2.1]oct-4-yl |
| 41 | " | N | 3,8-diazabicyclo[3.2.1]oct-8-yl |
| 42 | " | N | 3-amino-4-methyl-1-pyrrolidinyl (cis and trans mixture) |
| 43 | " | N | 4-aminomethyl-3-hydroxy-1-pyrrolidinyl |
| 44 | " | CH | 4-aminomethyl-3-hydroxy-1-pyrrolidinyl |
| 45 | " | N | (R)-3-amino-1-pyrrolidinyl |
| 46 | " | N | (S)-3-amino-1-pyrrolidinyl |
| 47 | " | N | cis-3-amino-4-methyl-1-pyrrolidinyl |
| 48 | " | N | trans-3-amino-4-methyl-1-pyrrolidinyl |

TABLE 2

| | UZ,13/20 MIC (mg/ml) | | | | | | |
|---|---|---|---|---|---|---|---|
| Ex. No. | S. aur. | S. faecal. | S. faeci. | E. coli | K. oxyto. | E. clo. | P. aer. |
| Nal. | 8.0 | >125 | >125 | 2.0 | 63.0 | 72.0 | 125.0 |
| Nor. | 0.25 | 1.0 | 8.0 | 0.13 | 0.25 | 0.5 | 0.5 |
| Cip. | 0.06 | 0.5 | 4.00 | 0.016 | 0.03 | 0.06 | 0.06 |
| 1 | 0.03 | 0.13 | 2.0 | 0.03 | 2.0 | 0.06 | 0.06 |
| 2 | 0.06 | 2.0 | —0.13 | 4.0 | 1.0 | 4.0 | |
| 6 | 0.03 | 0.5 | — 0.016 | 0.5 | 0.25 | 0.5 | |
| 7 | 0.13 | 1.0 | 2.0 | 0.5 | 2.0 | 0.25 | 2.0 |
| 8 | 0.25 | 4.0 | 16.0 | 0.5 | 2.0 | 0.5 | 1.0 |
| 9 | 0.03 | 0.25 | 0.5 | 0.5 | 2.0 | 0.25 | 0.5 |
| 10 | 0.06 | 0.5 | 2.0 | 0.5 | 4.0 | 0.5 | 8.0 |
| 11 | 0.06 | 1.0 | 4.0 | 0.06 | 0.06 | 0.03 | 1.0 |

TABLE 2-continued

| Ex. No. | S. aur. | S. faecal. | S. faeci. | E. coli | K. oxyto. | E. clo. | P. aer. |
|---|---|---|---|---|---|---|---|
| 12 | 0.25 | 2.0 | 4.0 | 0.13 | 1.0 | 0.25 | 4.0 |
| 13 | 0.13 | 2.0 | 4.0 | 0.13 | 2.0 | 0.25 | 2.0 |
| 14 | 0.5 | 2.0 | 2.0 | 0.25 | 2.0 | 0.25 | 0.5 |
| 15 | 0.13 | 2.0 | 4.0 | 0.25 | 8.0 | 0.5 | 8.0 |
| 16 | 0.25 | 8.0 | 16.0 | 0.06 | 1.0 | 0.25 | 4.0 |
| 17 | 0.06 | 0.25 | 0.5 | 0.25 | 1.0 | 0.25 | 6.0 |
| 20 | 0.06 | 0.5 | 4.0 | 0.016 | 0.5 | 0.06 | 1.0 |
| 21 | 0.06 | 2.0 | 4.0 | 0.03 | 0.25 | 0.06 | 1.0 |
| 22 | 0.03 | 1.0 | 4.0 | 0.06 | 1.0 | 0.25 | 0.5 |
| 23 | 0.03 | 0.5 | 2.0 | 0.13 | 0.5 | 0.06 | 1.0 |
| 24 | 0.03 | 0.5 | 1.0 | 0.25 | 2.0 | 0.25 | 1.0 |
| 25 | 0.03 | 0.25 | 0.5 | 0.25 | 1.0 | 0.5 | 1.0 |
| 26 | 0.13 | 2.0 | 8.0 | 0.25 | 1.0 | 0.25 | 2.0 |
| 30 | 0.06 | 0.51 | 0.5 | 0.06 | 0.06 | 0.06 | 0.25 |
| 32 | 0.25 | 2.0 | 4.0 | 0.5 | 2.0 | 0.25 | 4.0 |

The following abbreviations are used in Table 2
Nal = nalidixic acid
Nor = norfloxacin
Cip = ciprofloxacin
S. aur. = Staphylococcus aureus
S. faecal. = Streptococcus faecalis
S. faeci. = Streptococcus faecium
E. coli = Escherichia coli
K. oxyto. = Klebsiella oxytoca
E. clo. = Enterobacter cloacae
P. aer. = Pseudomonas aeruginosa

TABLE 3

| Ex. No. | S. aur. | S. faecal. | S. faeci. | E. coli | K. pneum. | E. clo. | P. aer. |
|---|---|---|---|---|---|---|---|
| Cip. | 0.13 | 0.5 | 8 | 0.015 | 0.03 | 0.008 | 0.13 |
| Nor. | 0.25 | 2 | 8 | 0.06 | 0.03 | 0.06 | 0.5 |
| 30 | 0.06 | 0.25 | 2 | 0.06 | 0.06 | 0.03 | 0.13 |
| 36 | 0.015 | 0.25 | 1 | 0.13 | 0.13 | 0.06 | 0.25 |
| 42 | 0.03 | 0.25 | 1 | 0.008 | 0.06 | 0.015 | 0.25 |
| 45 | 0.15 | 0.13 | 1 | 0.06 | 0.13 | 0.06 | 0.25 |
| 46 | 0.008 | 0.03 | 0.25 | 0.015 | 0.03 | 0.008 | 0.06 |
| 47 | 0.015 | 0.13 | 1 | 0.25 | 0.03 | 0.13 | 0.5 |
| 48 | 0.008 | 0.06 | 0.5 | 0.015 | 0.06 | 0.015 | 0.25 |

The following abbreviations are used in TABLE 3:
Nor = norfloxacin
Cip = ciprofloxacin
S. aur. = Staphylococcus aureus
S. faecal. = Streptococcus faecalis
S. faeci. = Streptococcus faecium
E. coli = Escherichia coli
K. pneum. = Klebsiella pneumoniae
E. clo. = Enterobacter cloaca
P. aer. = Pseudomonas aeruginosa

TABLE 4

TOXICOLOGIC TEST RESULTS & WATER SOLUBILITY

| EX. NO. | LD50 mg/kg | LD0 mg/kg | WATER SOLUBILITY mg/ml (pH iso) |
|---|---|---|---|
| Cip. | N/A | N/A | 0.07 |
| 30 | N/A | N/A | 0.08 |
| 46 | 350 | N/A | 0.01 |
| 47 | >1000 | >1000 | 0.03 |
| 48 | >1000 | >1000 | 0.24 |

The data set forth in Tables 2, 3 and 4 above show that the compounds described above as the most especially preferred, namely those compounds according to Formula I wherein $R^1$ is —C(CH$_3$)$_3$, X is F, Y is N, and Z is selected from

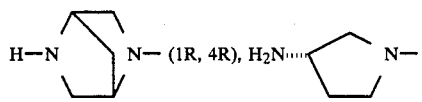

(racemic mixture, R-isomer and S-isomer), and

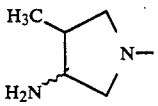

(racemic mixture, cis-isomer and trans-isomer), possess an especially advantageous broad spectrum of anti-bacterial activity. Among these compound, 7-(trans-3-amino-4-methylpyrrolidin-1-yl)-1-(1,1-dimethylethyl)-1,4-dihydro-6-fluoro-4-oxo-1,8-naphthyridine-3-carboxylic acid (methanesulfonate) (Ex. 48) is the most especially preferred because it has been shown to possess the most advantageous combination of anti-bacterial, toxicity, and water-solubility properties. A compound as named above except having a 7-[(1R, 4R)-2,5-diazabicyclo[2.2.1]heptan-2-yl group (Ex. 30) also possesses a highly advantageous combination of the above mentioned properties.

EXAMPLE

PREPARATION OF R- AND S-3-AMINO-PYRROLIDINE AND USE OF SAME TO PREPARE EXAMPLES 45 AND 46, RESPECTIVELY.

(S)-3-(4-METHYLSULFONYLOXY)-1-PHENYL-METHYL PYRROLIDINE

To a solution of 16.4 g (92.5 mmol) of (S)-3-hydroxy-1-phenylmethyl pyrrolidine (prepared according to KOJIMA, Y; TAKENAKA, T in J. Med. Chem. 1986, 29, 2504) in 164 ml pyridine cooled to +5° C. was added 19.35 g (101.7 mmol) of 4-toluenesulfonylchloride. The mixture was stirred 48 hours at +10° C. The solvent was removed and the residue was purified by chromatography using dichloromethane/acetone (95:5) to yield 18.80 g (63%) of title compound - M.P. 68° C., $[\alpha]_{20}^D = -30°$ C. (c=5, MeOH).

(R)-3-(4-METHYSULFONYLOXY)-1-PHENYL-METHYL PYRROLIDINE

This product was prepared as example above (starting from d-malic acid). M.P. 62° C., $[\alpha]_{20}^D = +31.2°$ (c=5, MeOH). Alternatively it was possible to prepare the (R) isomer from the (S) isomer by transforming (S)-3-(4-methylsulfonyloxy)-1-phenylmethyl pyrrolidine in (R)-3-acetyloxy-1-phenylmethyl pyrrolidine with tetraethyl ammonium acetate in ethyl acetate ($[\alpha]_{20}^D = +21.9°$, c=5, MeOH) which was successively hydrolyzed with aqueous sodium hydroxide and tosylated again at +5° C. in pyridine to give the title compound.

(R)-3-AZIDO-1-PHENYLMETHYL PYRROLIDINE

To a solution of 17.1 g (51.6 mmol) of (S)-3-(4-methysulfonyloxy)-1-phenylmethyl pyrrolidine in 200 ml anhydrous dimethylformamide preheated to 60° C. was added 33.5 g (516 mmol) of sodium azide. The mixture was stirred 7 hours to 60° C. Insoluble material was filtered off. The solvent was removed at 50° C. under reduced pressure. The residue was dissolved in ethyl acetate, washed twice with water and dried over magnesium sulfate to yield 7.95 g (76.5%) of title compound as an oil. $[\alpha]_{20}^D = -7.2°$ (c=5, MeOH)-IR (cm$^{-1}$): 2100.

(S)-3-AZIDO-1-PHENYLMETHYL PYRROLIDINE

The (S) isomer was basically prepared in the same way as the (R) isomer starting from the (R) tosyl pyrrolidine-$[\alpha]_{20}{}^D = +6.9°$ (c=5, MeOH).

(R)-3-AMINO-PYRROLIDINE, DIHYDROCHLORIDE

To a solution of 7.05 g (34.8 mol) of (R)-3-azido-1-phenylmethyl pyrrolidine and 34.8 ml aqueous 1N hydrochloric acid in 245 ml ethanol was added 3.5 g of 10% palladium on carbon. The mixture was hydrogenized for 30 mn. It was added 3.5 g more of the catalyst and the mixture hydrogenized again for 2 hours. The catalyst was filtered over a celite pad. It was added 34.8 ml aqueous 1N hydrochloric acid to the filtrat, which was evaporated under reduced pressure. The residue was taken up three times with 70 ml ethanol and the solvent removed each time. The dihydrochloride crystallized in the minimum amount of ethanol to give 4.45 g (80.5%) of title compound. $[\alpha]_{20}{}^D = -1.2°$ (c=5, 0.1N HCl).

(S)-3-AMINO-PYRROLIDINE, DIHYDROCHLORIDE

This compound was prepared exactly as described in the above procedure with the (S)-3-azido-1-phenylmethyl pyrrolidine. $[\alpha]_{20}{}^D = +1°$ (c=5; 0.1N HCl).

7-[(R)-3-AMINO-1-PYRROLIDINYL]-1-(1,1-DIMETHYLETHYL-1,4-DIHYDRO-6-FLUORO-4-OXO-1,8-NAPHTHYRIDINE-3-CARBOXYLIC ACID, ETHYL ESTER

To a suspension of 0.48 g (3.02 mmol) of (R)-3-amino-1-pyrrolidine, dihydrochloride and 0.76 g (2.30 mmol) of 1-(1,1-dimethylethyl)-1-1,4-dihydro-7-chloro-6-fluoro-4-oxo-1,8-naphthyridine-3-carboxylic acid, ethyl ester in 15 ml acetonitrile was added 1.40 g (9.26 mmol) of 1,8-diazabicyclo[5.4.0]undec-7-ene. The solution was heated one hour at +65° C. The reaction mixture was cooled in an ice-bath. The precipitate was filtered and dried to yield 0.77 g (89.5%) of title compound-M.P. 257° C. $[\alpha]_{20}{}^D = +73.5°$ (c=2, 0.1N HCl/MeOH 50:50).

7-[(S)-3-AMINO-1-PYRROLIDINYL]-1-(1,1-DIMETHYLETHYL)-1,4-DIHYDRO-6-FLUORO-4-OXO-1,8-NAPHTHYRIDINE-3-CARBOXYLIC ACID, ETHYL ESTER

The (S) isomer was prepared as described for (R) isomer as above. M.P. 257° C. $[\alpha]_{20}{}^D = -8.1°$.

7-[(R)-3-AMINO-PYRROLIDINYL]-1-(1,1-DIMETHYLETHYL)-1,4-DIHYDRO-6-FLUORO-4-OXO-1,8-NAPHTHYRIDINE-3-CARBOXYLIC ACID, METHANESULFONATE

A suspension of 6.60 g (17.5 mmol) of 7-[(R)-3-amino-1-pyrrolidinyl]-1-(1,1-dimethylethyl)-1,4-dihydro-6-fluoro-4-oxo-1,8-naphthyridine-3-carboxylic acid, ethyl ester in a solution of 70 ml 1N aqueous sodium hydroxide was heated under reflux for 20 mn. The solution was cooled and the pH was adjusted to 6.5 with 12N hydrochloric acid. The precipitate was filtered and dried to give 5.95 g of the amino-acid. M.P. 256° C., $[\alpha]_{20}{}^D = 24.4°$ (c=1, 0.1N HCl). This amino-acid was suspended in 60 ml methanol and heated under reflux. To this hot suspension was added 1.28 ml (19.8 mmol) of methanesulfonic acid and then 100 ml of methanol in order to get a solution at reflux. The solution was concentrated to 100 ml and kep in a refrigerator for 30 mn. The precipitate was filtered and dried to give 5.9 g (75.9%) of title compound. M.P. 255° C.; $[\alpha]_{20}{}^D = -18.6°$ (c=1, 0.1N HCl).

7-[(S)-3-AMINO-1-PYRROLIDINYL]-1-(1,1-DIMETHYL)-1,4-DIHYDRO-6-FLUORO-4-OXO-1,8-NAPHTHYRIDINE-3-CARBOXYLIC ACID, METHANESULFONATE.

This compound was prepared according to the procedure described above. M.P. 253°-254° C. $[\alpha]_{20}{}^D = +21.4°$ (c=1, 0.1N HCl).

EXAMPLE -

PREPARATION OF (1R, 4R)-2,5-DIAZABICYCLO-[2.2.1]-HEPTANE, DIHYDROBROMIDE

ALLO-4-HYDROXY-D-PROLINE HYDROCHLORIDE (1)

Ref: D. L. Baker, S. J. Fritschel, J. R. Stille and J. K. Stille, J. Org. Chem. (1981) Vol 46, pp. 2954–2960. $[\alpha]_D = +19.81°$ (c=2, H$_2$O)

ALLO-4-HYDROXY-D-PROLINE ETHYL ESTER HYDROCHLORID (2)

A slurry of 240 g (1.432 mole) mor Allo-4-hydroxy-D-Proline hydrochloride in 1.2 L of absolute ethanol was treated with dry hydrogene chloride until homogeneous. The solution was heated to the reflux temperature for 5 h. The mixture was kept at room temperature overnight, then cooled in an ice bath and the resulting precipitate was filtered, washed with acetone and dried under reduced pressure to yield 212.1 g (75%) of (2) M.P. −148° C. $[\alpha]_D = +20.37°$ (c=2, H$_2$O).

ALLO-1-(4-TOLUENESULFONYL)-4-(TOLUENESULFONYLOXY)-D-PROLINE ETHYL ESTER (3)

To a cold solution of 74 g (0.377 mole) of allo-4-hydroxy-D-proline Ethyl Ester Hydrochloride (2) and 38.1 g of triethylamine (0.377 mole) in pyridine (740 ml) at −5° C. there was added portionwise 158.2 g (0.83 mole) of 4-toluenesulfonyl chloride. The cold solution was stirred 1 h at 0° C., stored overnight in the refrigerator. Then the mixture was stirred at room temperature for 5 h, poured into ice water (550 ml). The precipitate was filtered, washed with water, dried to give 131 g (74.2%) of the titled compound. M.P. =125° C. $[\alpha]_D = +26.48°$ C. (c=2, CHCl$_3$)

4-(ACETYLOXY)-1-(4-TOLUENESULFOXYL)-D-PROLINE ETHYL ESTER (4)

To 350 ml of toluene were added 20 g (0.150 mole) of anhydrous tetramethylammonium acetate and 54.8 g (0.117 mole) of allo-1-(4-toluenesulfonyl)-4-(4-toluenesolfonlyloxy)-D-proline ethyl ester (3) under nitrogen. The mixture was refluxed overnight and then cooled. The organic layer was washed with water (2×100 ml), dried over magnesium sulfate, filtered and evaporated to dryness. The residue (40 g) was taken up with 80 ml of isopropanol. The mixture as stirred for 30 minutes at 0° C., the resulting crystalline product was collected, dried under reduced pressure to give 30.3 g (74%) of the title compound. M.P. =81° C. $[\alpha]_D = +82.64°$ (c=2, CHCl$_3$).

4-HYDROXY-1-(4-TOLUENESULFONYL)-D-PROLINE ETHYL ESTER (5)

To the suspension of 1665 g of compound (4) in 20 L of methanol there was added 8 L of distillated water. The pH was adjusted to 11–11.5 using sodium carbonate (~45 g). After 4 hours the pH was adjusted to 7 using acetic acid (~22,5 ml) and the mixture kept at room temperature overnight. At this time the pH was adjusted to 7 with another portion of acetic acid (2,5 ml), the solution volume was reduced by half by rotary evaporation. Then 20 L of water were added and the mixture was extracted with 2 portions of dichloromethane (15 L and 3 L). The combined extracts were washed with water (5 L), dried over magnesium sulfate, filtered and evaporated under reduced pressure to give 1444,4 g of an oily product (98%). [α]= +100.35° (c=1.8, EtOH). K.F. −0.78%.

4-HYDROXY-1-(4-TOLUENESULFONYL)-D-PROLINOL (6)

To an ice-cold solution of 286.4 g (0.914 mole) of 4-hydroxy-(4-toluenesulfonyl)-D-proline ethyl ester (5) in 2.8 L of tetrahydrofuran was added 20 g (0.918 mole) of lithium borohydride in one portion. The mixture was stirred at 0° C. for 1 hour and then kept at a temperature below 25° C. overnight. The mixture was cooled to 0° C. and the pH adjusted to 3 with 6N hydrochloric acid (180 ml). The volume was reduced to 500 ml by rotary evaporation, and 1.5 L of water was added. The white precipitate was filtered, washed with cold water (500 ml) dried under reduce pressure to give 223.8 g (90%) of the title compound. M.P. =127° C. [α]$_D$=36.66° (c=1.0, acetone) K.F. −6.55%.

(2R, 4S)-1-(4-TOLUENESULFONYL)-2-(4-TOLUENESULFONYLOXYMETHYL)-4-(4-TOLUENESULFONYLOXY)-PYRROLIDINE (7)

To an ice-cold solution of 219.2 g (0.808 mole) of 2R, 4S-1-(4-toluenesulfonyl)-2-hydroxymethyl-4-hydroxypyrrolidine (6) in 1 L of pyridine were added 539.2 g (2.828 mole) of 4-toluenesulfonyl chloride in one portion. The temperature rose to 50° C. The mixture was cooled at 10° C. and kept for 2 hours at this temperature and then at room temperature overnight. The mixture was pured into 5 L of 2.4N hydrochloric acid. After cooling, a precipitate was collected, washed with cold water, dried under reduced pressure. This presicpitate was taken up with 1 L of ethanol, filtered and washed with cold ethanol, dried under reduce pressure to give 406 g (86%) of the titled compound. M.P. =134° C. [α]$_D$= +57.13° (c=1.9, acetone).

(1R, 4R)-2-(4-TOLUENESULFONYL)-5-PHENYLMETHYL-2,5-DIAZABICYCLO-[2.2.1]-HEPTANE (8)

A mixture of 2697 g (4.653 moles) of (2R, 4S)-1-(4-toluenesulfonyl)-2-(4-toluenesulfonyloxymethyl)-4-(4-toluenesulfonyloxy)-pyrrolidine and 1640 g (15.304 moles) of benzylamine in 15 L of toluene was heated under reflux. After 6 hours 100 g of benzylamine were added and the reflux continued for 3 hours. The mixture was cooled, filtered and the residue was washed with 5 L of toluene. The combined organic layers were evaporated to dryness and the resulting solid was taken up with 2 L of isopropanol. After cooling the product was filtered, washed with cold isopropanol and dried under reduced pressure to give 1434 g of the titled compound. (90%). M.P. =124° C. [α]$_D$= −15.72° (c=1.6, acetone)

(1R, 4R)-5-PHENYLMETHYL-2,5-DIAZABICYCLO-[2.2.1]-HEPTANE, DIHYDROBROMIDE (9)

To a hot solution of 2.85 L of hydrobromic acid 33% in acetic acid* at 70° C. there was added 1428 g (4.17 moles) of (1R, 4R)-2-(4-toluenesulfonyl)-5-phenylmethyl-2,5-diazabicyclo-[2.2.1]-heptane (8). The solution was stirred for 12 h. The resulting suspension was cooled (18°-20° C.). The precipitate was filtered, washed with diisopropylether and dried at 40° C. under reduced pressure to give 1294 g (89%) of the titled compound. M.P. =276° C. [α]$_D$= −0.38° (c=1, H$_2$O).

* and 14 L of acetic acid.

(1R, 4R)-2,5-DIAZABICYCLO-[2.2.1]=HEPTANE, DIHYDROBROMIDE (10)

A suspension of 76 g (0.217 moles) of (1R, 4R)-5-phenylmethyl-2,5-diazabicyclo-[2.2.1]-heptane, dihydrobromide (9) and 37 g of 10% Pd on C in 1.2 L of water was hydrogenated at atmospheric pressure at 40° C. The reaction was completed within 8 hours. The catalyst was filtered off and the filtrate was evaporated under reduced pressure. The residue was taken up with ethanol and the resulting precipitate was filtered to give 51.4 g (91%) of the titled compound. M.P. =285°. [α]$_D$= −19.83 (c=1.2, 0.1N HCl).

3(R)-N',N'-DIMETHYLHYDRAZINO-1-PHENYLMETHYL PYRROLIDINE, 4-METHYLPHENYLSULFONIC ACID SALT

To a solution of 3.96 g (12 mmoles) of 3(S)-(4-methylphenylsulfonyloxy)-1-phenylmethyl pyrrolidine in 40 mL anhydrous methanol was added 2.15 g (36 mmoles) of N,N-dimethylhydrazine. The solution was heated under reflux for 9 hours. Then, the solvent was evaporated. The residue was taken up with dichloromethane and brine, the organic layer was dried over MgSO$_4$ to give 2.4 g of crude product which was recrystallizedin ethyl acetate to afford 1.61 g of title compound. Yield 36%.

3(R)-N',N'-DIMETHYLHYDRAZINO-PYRROLIDINE, DIHYDROCHLORIDE

A suspension of 0.82 g (2.1 mmoles) of 3(R)-N',N'-dimethylhydrazino-1-phenylmethyl pyrrolidine, 4-methylphenylsulfonic acid salt and 700 mg Pd 10% on C in 20 mL ethanol was hydrogenolyzed at atmospheric pressure for one hour. The catalyst was filtered off and the solvent was evaporated from the filtrate, and the residue was taken up in 4 mL isopropanol to which was added 750 mL of 5N hydrochloric acid in ethanol. The precipitate was filtered to give 440 mg of title compound. Yield 97%.

7-[3(R)-N',N'-DIMETHYLHYDRAZINO-PYRROLIDIN-1-YL]-1-(1,1-DIMETHYLETHYL)-6-FLUORO-1,4-DIHYDRO-4-OXO-1,8-MAPHTYRIDINE-3-CARBOXYLIC ACID, DIHYDROCHLORIDE

This compound was prepared essentially as described in example 30. Yield 76,7%. M.P. >270° C.; [α]$_{20}$$^D$= −14.97° (c=0.2, H$_2$O)

3(R)-[4-METHYLPIPERAZINYL]-1-PHENYLMETHYL PYRROLIDINE, DIHYDROCHLORIDE

To a solution of 3.31 g (10 mmoles) of 3(S)-4-methylphenylsulfonyloxy-1-phenylmethyl pyrrolidine in 13 mL anhydrous methanol was added 2.0 g (20 mmoles) of N-methylpiperazine. The solution was heated under reflux overnight. After evaporation of solvent the residue was taken up in 20 mL anhydrous ether. Insoluble material was filtered off and the filtrate evaporated to give 1.68 g of an oil which was transformed in to his dichlorhydrate in isopropanol with ethanolic hydrochloric acid to yield 1.25 g of title compound. M.P. 279°-80° C. dec. Yield 38%. [α]$_{20}$$^D$=1,76° (c=5, MeOH).

3(R)-[4-METHYLPIPERAZIN-1-YL]-PYRROLIDINE, DIHYDROCHLORIDE

A suspension of 1.55 g (0.46 mmole) of 3(R)-[4-methylpiperazin-1-yl]-1-phenylmethye pynolidine, dihydrochloride and 0.48 g 10% Pd on C in 20 mL water was hydrogenolyzed at atmospheric pressure. The reaction was complete in about 4 hours. The catalyst was filtered off and the solvent was evaporated from the filtrate and the residue was triturated in ethanol to give 0.85 g (Yield 75%) of the title compound.

7-[3(R)-(4-METHYLPIPERAZIN-1-YL)-PYR-ROLIDINYL]-1-(1,1-DIMETHYLETHYL)-6-FLUORO-1,4-DIHYDRO-4-OXO-1,8-NAPH-TYRIDINE-3-CARBOXYLIC ACID, HYDROCHLORIDE, MONOHYDRATE

This compound was prepared basically as described in example 30. Yield 65%; M.P. 259°-60° C.; $[\alpha]_{20}{}^D = 14{,}3°$ (c=0.2%, H$_2$O).

EXAMPLE -

SYNTHESIS OF 7-PIPERAZINYL-6-FLUORO-1,4-DIHYDRO-1-(1-METHYLETHENYL)-4-OXO-1,8-NAPHTHYRIDINE CARBOXYLIC ACID:

3-(2,6-DICHLORO-3-FLUORO-5-PYRIDINYL-3-OXO-2-(((2-PHENYLTHIO-1-MEHYLETHYL)AMINO)METHYLENE)-PROPANOCI ACID ETHYLESTER 2.09 g (12.5 mmoles) of 2-amino-1-benzenethiopropane was added to a suspension of 4 g (12 mmoles) of 3-(2,6-dichloro-3-fluoro-5-pyridinyl)-3-oxo-2-ethoxymethylenepropanoic acid ethylester in 10 ml dry ethanol at −8° under nitrogen.

The mixture was stirred at room temperature for two and half hours. The precipitated product was filtered, washed with EtOH, dried in vacuo to afford 3.93 of titled compound. MP 69°-70° C.

7-FLUORO-6-CHLORO-1,4-DIHYDRO-1-(2-PHENYLTHIO-1-METHYLETHYL)-4-OXO-1,8-NAPHTHYRIDINE-3-CARBOXYLIC ACID ETHYLESTER

There was gradually added 0.4 g (10 mmoles) of 60% NaH under nitrogen to a solution of 3.92 g (8.55 mmoles) of 3-(2,6-dichloro-3-fluoro-5-pyridyl)-3-oxo-2-(((2-phenylthio-1-methylethyl) amino) methylene)-propanoic acid ethylester with external cooling to keep the temperature below 40° C. After stirring for 25 min. at room temperature, the solvent was eliminated in vacuo.

The resulting mixture was taken up with 50 ml dichloromethane and 10 g ice. After decantation, inorganic layer was extracted with dichloromethane (3×10 ml). The collected organic layer was washed with water (10 ml) and dried over magnesium sulfate to afford 3.5 g of a product which was triturated with 50 ml of diisopropyloxide to give 2.75 g of titled compound. MP 70° C.

7-FLUORO-6-CHLORO-1,4-DIHYDRO-1-(2-PHENYLSULFINYL-1-METHYLETHYL-4-OXO-1,8-NAPHYTHYRIDINE-3-CARBOXYLIC ACID ETHYLESTER

There was gradually added 1.03 g (6 mmoles) of metachloroperbenzoic acid to a solution of 2.88 g (5.25 mmoles) of 7-fluoro-6-chloro-1,4-dihydro-1-(2-phenylthio-1-methylethyl)-4-oxo-1,8-naphthyridine-3-carboxylic acid ethylester at 5° C.

After stirring for 30 min. at room temperature, 25 ml of 10% sodium-bicarbonate was added. The aquous phase was extracted with dichloromethane (2×10 ml). The collected organic phases were washed with water, dried over magnesium sulfate.

The residue (2.26 g) was chromatographed over silica gel using ethylacetate as eluant to give 1,5 g of titled compound. MP 170°-2° C.

7-PIPERAZINYL-6-FLUORO-1,4-DIHYDRO-1-(2-PHENYLSULFINYL-1-METHYLETHYL)-4-OXO-1,8-NAPHTHYRIDINE-3-CARBOXYLIC ACID ETHYLESTER

To a suspension of 2.47 g (5.65 mmoles) of 7-chloro-6-fluoro-1,4-dihydro-1-(2-phenylsulfinyl-1-methylethyl)-4-oxo-1,8-naphthyridine-3-carboxylic acid ethylester in 70 ml acetonitrile was added 1.95 g (22.6 mmoles) piperazine and the resulting mixture was stirred for one and half hours at room temperature.

After evaporation to dryness, the residue was taken up with water, extracted with dichloromethane (3×40 ml). This organic phase was washed with 15 ml water, dried over magnesiumsulfate. Evaporation of dichloromethane gave 2.66 g of a product which was triturated 50 ml ethylether to yield 2.46 g of titled compound. The purity was checked by tlc (methanol-dichloromethane 20/80).

7-PIPERAZINYL-6-FLUORO-1.4-DIHYDRO-1-(1-METHYLETHENYL)-4-OXO-1,8-NAPHTHYRIDINE CARBOXYLIC ACID

A mixture of 0.63 g (1.58 mmoles) of 7-piperazinyl-6-fluoro-1,4-dihydro-1-(1-methylethenyl)-4-oxo-1,8-naphthyridine carboxylic acid ethylester hydrochloride and 4 ml 2N sodium hydroxyde was heated under reflux for 1 hr 40 min.

After cooling, the pH was adjusted to 7.3 with 2N hydrochloric acid. The precipitated solid was filtered, washed with water, taken up with 10 ml boiling methanol, cooled and filtered again. This filtered compound was recristallized in 15 mL dimethylformamid-water 10:5 to yield 0.18 g of titled compound. MP 234° C.

EXAMPLE -

SYNTHESIS OF 7-PIPERAZINYL-6-FLUORO-1,4-DIHYDRO-4-OXO-1-(1-METHYLETHENYL)-3-QUINOLINECARBOXYLIC ACID 3-(2,4-DICHLORO-5-FLUOROPHENYL)-3-OXO-2-(((2-DIMETHYLAMINO-1-METHYLETHYL)AMINO) METHYLENE)-PROPANOIC ACID ETHYLESTER

A solution of 1.29 ml (10 mmoles) of 1-methyl-1-(dimethylamino)ethylamine in 5 mL ethanol was added during 10 min. to a solution of 3.35 g (10 mmoles of 3-(2,4-dichloro-5-fluorophenyl)-3-oxo-2-(ethoxymethylene)propanoic acid ethylester in 10 mL ethanol at −8° C.

After stirring for 2 hr 30 min. at room temperature the mixture was evaporated to dryness to give 3.98 g of the titled compound as an oil.

7-CHLORO-6-FLUORO-1,4-DIHYDRO-1-(2-(DIMETHYLAMINO)-1-METHYLETHYL)-4-OXO-3-QUINOLINE CARBOXYLIC ACID ETHYLESTER

To a solution of 10 mmoles of 3-(2,4-dichloro-5-fluorophenyl)-3-oxo-2-(((2-(dimethylamino)-1-methylethyl) amino) methylene)-propanoic acid ethylester in 40 ml dioxanne was added 0.5 g (12 mmoles of 60% NaH in one portion.

The mixture was heated under reflux for two hours, evaporated to dryness and taken up with diethylether and water. The organic layer gave 3.3 g crude product which was dissolved in 29 ml acetone. To this solution was added an excess of 5N ethanolic hydrochloric acid. The resulting hydrochloride was filtered and washed with acetone.

1.77 g of this hydrochloride was dissolved in 35 ml water and sodium hydroxyde was added to obtain pH>11. After saturating with sodium hydrochloride, this solution was extracted with diethylether. The solvent was evaporated to dryness to afford 1.22 g titled compound (amorphous solid).

7-CHLORO-6-FLUORO-1,4-DIHYDRO-1-(2-(DIMETHYLAMINO)-1-METHYLETHYL)-4-OXO-3-QUINOLINE CARBOXYLIC ACID

A suspension of 1,8 mmoles of 7-chloro-6-fluoro-1,4-dihydro-1-(2-dimethylamino)-1-methylethyl)-4-oxo-3-quinoline carboxylic acid ethylester in 2.5 mL N NaOH was heated under reflux for 2 hours.

After cooling, the mixture was washed with ethylacetate (2×2 mL) and pH was adjusted to 6–6, 5 with hydrochloric acid. The precipitated compound was filtered, washed with 2 mL water, 2 mL ethylacetate, 2×5 mL petroleum ether to give 0.31 g titled compound. MP 238° C.

N,N,N-TRIMETHYL-2-(3-(ETHOXYCARBONYL)-7-CHLORO-6-FLUORO-4-OXO-1,4-DIHYDRO-1-QUINOLEINYL)-PROPANAMINIUM IODINE

To a solution of 1.2 g (3.35 mmole) of 7-chloro-6-fluoro-1,4-dihydro-1-(2-(dimethylamino)-1-methylethy)-4-oxo-3-quinolinecarboxylic acid ethylester in 10 mL acetone was added 2.1 mL (33.5 mmoles) of methyliodide. The mixture was stirred for 5 hours at room temperature and 5 ml diethylether was added to help the precipitation.

The precipitate was filtered and washed with diethylether to give 1.80 g titled compound. MP 210° C.

7-CHLORO-6-FLUORO-1,4-DIHYDRO-4-OXO-1-(1-METHYLETHENYL)-3-QUINOLINE CARBOXYLIC ACID METHYLESTER

A hot solution of 2,4 g of N,N,N-trimethyl-2-(3-ethoxycarbonyl)-7-chloro-6-fluoro-4-oxo-1,4-dihydro-1-quinoleinyl)-propanaminium iodide in 75 mL methanol was treated twice with Dowex 1 (OH form) (prepared from 9.6 g Dowex 1 (Cl form)). The resin was washed with 30 ml methanol. The methanol was evaporated in vacuo and the residue was treated for one hour at 190° C. in vacuo.

The resulting product was chromatografied over silicagel using chloroform-methanol 97:3. The crude methylester was triturated in boiling diisopropylether. After cooling the solvent was eliminated by filtration to yield 0.3 g titled compound. RF =0.41 (chloroform-methanol 97:3).

7-CHLORO-6-FLUORO-1,4-DIHYDRO-4-OXO-1-(1-METHYLETHENYL)-3-QUINOLINE CARBOXYLIC ACID

A mixture of 0.3 g (1.07 mmoles) of 7-chloro-6-fluoro-1,4-dihydro-4-oxo-1-(1-methylethenyl)-3-quinoline carboxylic acid methylester, 1 mL methanol and 2.14 mL (2.14 mmoles) of normal sodium hydroxyde was heated under reflux for one and half hours. More sodium hydroxide (1 ml) was added and the heat was continued for 30 min.

The solution was diluted with 2 mL water, acified with 6N hydrochloric acid, satured with sodium chloride, extracted with ethylacetate and dried over magnesium sulfate to give 0.25 titled compound. MP 229° C.

6-FLUORO-1,4-DIHYDRO-7-PIPERAZINYL-4-OXO-1-(1-METHYLETHENYL)-3-QUINOLINE CARBOXYLIC ACID

A mixture of 0.25 g (0.89 mmole) of 7-chloro-6-fluoro-1,4-dihydro-1-(1-methylethenyl)-4-oxo-3-quinoline carboxylic acid, 0.38 g (4.45 mmoles) of piperazine and 2.1 mL N-Methylpyrrolidine was heated at 100° C. for 3 hours 30 min.

The final cooled mixture was diluted with 16 mL diethylether. The precipitated product was crystallized in 3.5 mL methanol to give 0.17 g titled compound. RF =0.3. (Methanol - chloroform - ammoniac 4:6:1).

The following shows additional compounds within the scope of the invention. TABLE 5 which may be prepared, by following substantially the procedure described in Example 30 except for substituting varying amino reactants for that used in Example 30. The symbol "*" designates compounds that have been prepared.

TABLE 5
LIST OF ADDITIONAL EXAMPLES

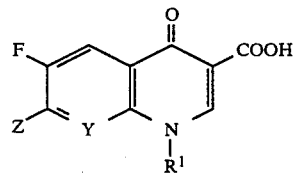

| Ex. | $R^1$ | Y | Z |
|---|---|---|---|
| 49 | C(CH₃)₃ | N | 3-aminomethyl-4-fluoro-1-pyrrolidinyl (cis & trans) |
| 50* | " | N | 3-aminomethyl-4-fluoro-1-pyrrolidinyl (cis) |
| 51* | " | N | 3-aminomethyl-4-fluoro-1-pyrrolidinyl (trans) |
| 52 | " | N | 3-amino-4-fluoro-1-pyrrolidinyl (cis & trans) |
| 53 | " | N | 3-amino-4-fluoro-1-pyrrolidinyl (cis) |
| 54 | " | N | 3-amino-4-fluoro-1-pyrrolidinyl (trans) |
| 55* | " | N | 3-methylamino-1-pyrrolidinyl |
| 56* | " | N | 3-ethylamino-1-pyrrolidinyl |
| 57* | " | N | 3-dimethylamino-1-pyrrolidinyl |
| 58* | " | N | 3-(R)-(4-methylpiperazin-1-yl)-1-pyrrolidinyl |
| 59* | " | N | 3-(R)-N',N'-dimethylhydrazino-pyrrolidin-1-yl |
| 60 | " | N | 3-(iminomethyl)amino-1-pyrrolidinyl |
| 61* | " | N | 3-imino-1-pyrrolidinyl |
| 62 | " | N | 3-(aminoiminomethyl)amino-1-pyrrolidinyl |
| 63 | " | N | 2-methyl-4-amino-1-pyrrolidinyl (cis & trans) |

TABLE 5-continued
LIST OF ADDITIONAL EXAMPLES

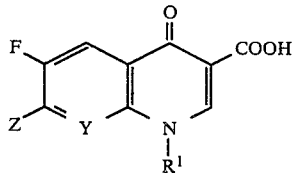

| Ex. | R¹ | Y | Z |
|---|---|---|---|
| 64 | " | N | 2-methyl-4-amino-1-pyrrolidinyl (cis) |
| 65 | " | N | 2-methyl-4-amino-1-pyrrolidinyl (trans) |
| 66 | " | N | 3-hydroxyamino-1-pyrrolidinyl |
| 67 | " | N | 3-hydroxyimino-1-pyrrolidinyl |
| 68 | " | N | 3-(N-cyano)amino-1-pyrroldinyl |
| 69 | " | N | 2,6-diazabicyclo[3.2.0]heptan-6-yl |
| 70 | " | N | 2-methyl-2,6-diazabicyclo[3.2.0]heptan-6-yl |
| 71 | " | N | 3-(R)-amino-4-(R)-ethyl-1-pyrrolidinyl |
| 72 | " | N | 3-(R)-amino-4-(S)-ethyl-1-pyrrolidinyl |
| 73 | " | N | 3-(S)-amino-4-(R)-ethyl-1-pyrrolidinyl |
| 74 | " | N | 3-(S)-amino-4-(S)-ethyl-1-pyrrolidinyl |
| 75 | " | N | 2-(R)-methyl-3-(R)-amino-1-pyrrolidinyl |
| 76 | " | N | 2-(R)-methyl-3-(S)-amino-1-pyrrolidinyl |
| 77 | " | N | 2-(S)-methyl-3-(R)-amino-1-pyrrolidinyl |
| 78 | " | N | 2-(S)-methyl-3-(S)-amino-1-pyrrolidinyl |
| 79 | " | N | 3-(R)-amino-4-(R)-phenyl-1-pyrrolidinyl |
| 80 | " | N | 3-(R)-amino-4-(S)-phenyl-1-pyrrolidinyl |
| 81 | " | N | 3-(S)-amino-4-(R)-phenyl-1-pyrrolidinyl |
| 82 | " | N | 3-(S)-amino-4-(R)-phenyl-1-pyrrolidinyl |
| 83 | C(CH₃)₂CH₂F | N | 3-(S)-amino-1-pyrrolidinyl |
| 84 | " | N | trans-3-aminomethyl-4-fluoro-1-pyrrolidinyl |
| 85 | " | N | trans-3-amino-4-methyl-1-pyrrolidinyl |
| 86 | —C(CH₃)CH₂CH₂ (ring) | N | 1-piperazinyl |
| 87 | —C(CH₃)CH₂CH₂CH₂ (ring) | N | 1-piperazinyl |

What is claimed is:

1. A compound having the formula

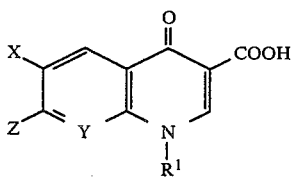

wherein:
$R^1$ is —C(CH$_3$)$_3$ optionally substituted by 1–3 fluorine atoms;
X is a member of the group selected from F, Cl, Br, CF$_3$, and CCl$_3$;
Y is N; and
Z is

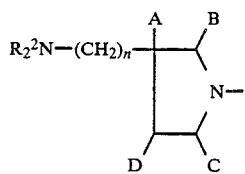

wherein each $R^2$ is independently selected from H, unsubstituted and substituted alkyl having 1 to 6 carbon atoms wherein the substituent is independently selected from 1–3 hydroxy, fluoro, chloro, amino, alkylamino, trifluoroacetylamino, and phenyl groups; cycloalkyl having 3 to 6 carbon atoms, and cycloalkenyl having 3 to 6 carbon atoms; and wherein A, B, C, and D, are independently selected from H; unsubstituted and substituted lower alkyl having 1 to 4 carbon atoms wherein the substituent is independently selected from 1-3 hydroxy, fluoro, chloro, amino, alkylamino, trifluoroacetylamino, and phenyl groups; amino; hydroxy; fluoro; chloro; and phenyl groups; and wherein n is selected from the integers 0, 1, 2, and 3, and wherein when each of the $R^2$ is other than H, the $R^2$ group is independently selected from CH$_3$ and C$_2$H$_5$,
and pharmaceutically acceptable acid addition and base salts thereof.

2. A compound according to claim 1 wherein X is F.

3. A compound according to claim 2 wherein and each $R^2$ is independently selected from H, CH$_3$, C$_2$H$_5$,

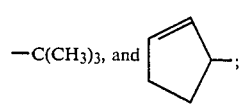

A, B, C, and D are independently selected from H, CH$_3$, and C$_2$H$_5$; and n is selected from 0, 1, and 2.

4. A compound according to claim 3 wherein $R^1$ is selected from —C(CH$_3$)$_3$, —C(CH$_2$F)(CH$_3$)$_2$, —C(CH$_2$F)$_2$CH$_3$, and —C(CF$_3$)(CH$_3$)$_2$.

5. A compound according to claim 4 wherein $R^1$ is —C(CH$_3$)$_3$.

6. A compound according to claim 5 wherein Z is selected from

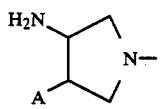

(A=H, (S) and (R); CH$_3$, cis and trans).

7. A compound according to claim 6 wherein Z is

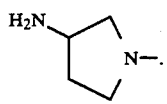

8. A compound according to claim 7 wherein Z is

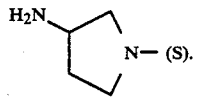

9. A compound according to claim 6 wherein Z is

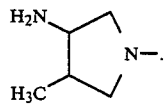

10. A compound according to claim 9 wherein Z is

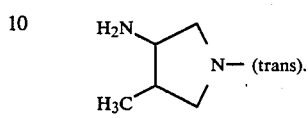

11. A pharmaceutical composition comprising an antibacterially effective amount of a compound according to claim 1 and a pharmaceutically acceptable carrier.

12. A composition according to claim 11 wherein the antibacterially effective amount of said compound comprises from about 0.5% to about 90% by weight of the composition.

13. A method of combatting bacterial infection in warm-blooded animals comprising administering to said animals an antibacterially effective amount of a compound according to claim 1.

14. A method according to claim 13 wherein the antibacterially effective amount of said compound comprises about 0.1 to about 15 mg/kg of body weight/day.

15. A method of combatting bacterial infection in warm-blooded animals comprising administering to said animals an antibacterially effective amount of a compound according to claim 6.

16. A method of combatting bacterial infection in warm-blooded animals comprising administering to said animals an antibacterially effective amount of a compound according to claim 10.

* * * * *